(12) United States Patent
Caimi et al.

(10) Patent No.: US 8,476,048 B2
(45) Date of Patent: Jul. 2, 2013

(54) **XYLOSE UTILIZING *ZYMOMONAS MOBILIS* WITH IMPROVED ETHANOL PRODUCTION IN BIOMASS HYDROLYSATE MEDIUM**

(75) Inventors: Perry G Caimi, Kennett Square, PA (US); William D Hitz, Wilmington, DE (US); Barry Stieglitz, Wynnewood, PA (US); Paul V Viitanen, West Chester, PA (US)

(73) Assignee: E I du Pont de Nemours and Company, Wilmington, DE (US)

(*) Notice: Subject to any disclaimer, the term of this patent is extended or adjusted under 35 U.S.C. 154(b) by 9 days.

(21) Appl. No.: 13/316,597

(22) Filed: Dec. 12, 2011

(65) Prior Publication Data
US 2012/0329114 A1   Dec. 27, 2012

Related U.S. Application Data

(60) Provisional application No. 61/424,077, filed on Dec. 17, 2010.

(51) Int. Cl.
*C12P 7/06* (2006.01)
(52) U.S. Cl.
USPC ............................................. 435/161
(58) Field of Classification Search
None
See application file for complete search history.

(56) References Cited

U.S. PATENT DOCUMENTS

| | | | |
|---|---|---|---|
| 5,231,020 A | 7/1993 | Jorgensen et al. | |
| 5,514,583 A | 5/1996 | Picataggio et al. | |
| 5,712,133 A | 1/1998 | Picataggio et al. | |
| 5,843,760 A | 12/1998 | Zhang et al. | |
| 6,566,107 B1 | 5/2003 | Zhang | |
| 7,223,575 B2 | 5/2007 | Zhang et al. | |
| 7,741,119 B2 | 6/2010 | Viitanen et al. | |
| 2003/0162271 A1 | 8/2003 | Zhang et al. | |
| 2007/0031918 A1 | 2/2007 | Dunson et al. | |
| 2008/0081358 A1 | 4/2008 | Dunson et al. | |
| 2008/0187973 A1 | 8/2008 | Vitanen et al. | |
| 2008/0286870 A1 | 11/2008 | Viitanen et al. | |
| 2009/0203099 A1 | 8/2009 | Caimi et al. | |
| 2009/0221078 A1 | 9/2009 | Caimi et al. | |
| 2009/0246846 A1 | 10/2009 | Viitanen et al. | |
| 2009/0246876 A1 | 10/2009 | Viitanen et al. | |
| 2011/0014670 A1 | 1/2011 | Caimi et al. | |
| 2011/0143408 A1 | 6/2011 | Yang | |
| 2011/0318801 A1 | 12/2011 | Kahsay et al. | |
| 2012/0178976 A1* | 7/2012 | Hennessey et al. | ............ 568/913 |

FOREIGN PATENT DOCUMENTS

| | | |
|---|---|---|
| WO | 9528476 A1 | 10/1995 |
| WO | 2004081185 A2 | 9/2004 |
| WO | 2008051349 A2 | 5/2008 |
| WO | 2009132201 A2 | 10/2009 |
| WO | 2011137150 A1 | 11/2011 |

OTHER PUBLICATIONS

Feldmann et al., Pentose Metabolism in Zymomonas Moblis Wild-Type and Recombinant Strains, Appl. Microbiol. Biotechnol., 1992, vol. 38:354-361.

Lawford et al., Comparative Energetics of Glucose and Xylose Metabolism in Recombinant Zymomonas Mobilis, Applied Biochemistry and Biotechnology, 2000, vol., 84-86;277-293.
Joachimsthal et al., Characterization of a High-Productiity Recombinant Strain of Zymomonas Mobilis for Ethanol Production From Glucose/Xylose Mixtures, Applied Biochemistry and Biotechnology, 2000, pp. 343-356, vol. 84-86.
Kim et al., Nuclear Magnetic Resonance Studies of Acetic Acid Inhibition of Rec Zymomonas Mobilis ZM4(pZB5) Applied Biochemistry and Biotechnology, 2000, vol. 84-86;pp. 357-370.
Joachimsthal et al., A Mutant of Zymomonas Mobilis ZM4 Capable of Ethanol Production From Glucose in the Presence of High Acetate Concentrations, Biotechnol. Lett., 1998 vol. 20:137/142.
Jeon et al., Kinetic Analysis of Ethanol Production by an Acetate-Strain of Recombinant Zymomonas Mobilis, Biotechnol. Lett., 2002, vol. 24:819-824.
J. Sambrook et al., Molecular Cloning: A Laborabory Manual, 1989, pp. 9.50-9.51, 11.7-11.8, 11.12-11.13, Second Edition, Cold Spring Harbor Laborabory: Cold Spring Harbor, New York.
F. M. Ausubel et al., Current Protocols in Molecular Biology, 1987, pp. 1.81-1.8.10, Greene Publishing and Wiley-Interscience.
Lawford, Hugh G. et al., Fermantation Performance Characteristics of a Prehydrolyzate-Adapted Xylose-Fermenting Recombinant Zymomonas in Batch and Continuous Fermentations, Applied Biochemistry and Biotechnology, 1999, pp. 191-204, vol. 77-79.
National Center for Biotechnology Information General Identifier No. 56542470, Jan. 25, 2005, J. S. Seo et al., The Genome Sequence of the Ethanologenic Bacterium Zymomonas Mobilis ZM4, Genbank AE008692.
Arfin et al., Global Gene Expression Profiling in *Escherichia coli* K12, J. Biol. Chem., 2000, vol. 275:29672-29684.
Arnold et al., Global Analysis of *Escherichia coli* Gene Expression During the Acetate-Induced Acid Tolerance Response, J. Bacteriol., 2001, vol. 183:2178-2186.
National Center for Biotechnology Information General Identifier No. 16129668, Aug. 8, 2009, M. Riley et al., *Escherichia coli* K-12; A Cooperatively Developed Annotation Snapshot-2005, Genbank NP_416227.
National Center for Biotechnology Information General Identifier No. 148556459, Apr. 29, 2009, A. Copeland et al., Complete Sequence of Chromosome of Sphingomonas WITTICHII RW1, Genbank YP_001264041.
L. R. Lynd et al., Microbial Cellulose Utilization: Fundamentals and Biotechnology, Microbiol. Mol. Biol. Rev., 2002, vol. 66:506-577.
Agrawal, Growth Inhibition of Zymomonas Mobilis ATCC 10988 by Ammonium Lons, Biotechnology and Bioengineering, 1989, vol. 34:278-281.
Crueger et al., A Textbook of Industrial Microbiology, 1989, Second Edition, Chapter 5, pp. 64-74, Sinauerassociates, Inc., Sunderland, MA.
Deshpande et al., Ethanol Production From Cellulose by Coupled Saccharification/Fermentation Using *Saccharomyces cerevisiae* and Cellulase Complex From Sclerotium Rolfsii UV-8 Mutant, Appl. Biochem. Biotechnol., 1992, vol. 36:227-234.

(Continued)

*Primary Examiner* — Suzanne M Noakes

(57) ABSTRACT

Xylose-utilizing, ethanol producing strains of *Zymomonas mobilis* with improved performance in medium comprising biomass hydrolysate were isolated using an adaptation process. Independently isolated strains were found to have independent mutations in the same coding region. Mutation in this coding may be engineered to confer the improved phenotype.

6 Claims, 4 Drawing Sheets

OTHER PUBLICATIONS

Mohagheghi, Ali et al., Performance of a Newly Developed Integrant of *Zymomonas mobilis* for Ethanol Production on Corn Stover Hydrolysate, Biotechnology Letters, 2004, pp. 321-325, vol. 26.

National Center for Biotechnology Information General Identifier No. 58255, Nov. 14, 2006, The Nucleotide Sequence of PACYC184, Genbank X06403.

Seo et al., The Genome Sequence of the Ethanologenic Bacterium *Zymomonas mobillis* ZM4, Nature Biotechnology, 2005, vol. 23:63-68.

Delgenes, J. P. et al., Effects of Lignocellulose Degrdation Products on Ethanol Fermentations of Glucose and Xylose by *Saccharomyces cerevisiae, Zymomonas mobilis, Pichia stipitis*, and *Candida shehatae*, Enzyme and Microbial Technology, 1996, pp. 220-225, vol. 19.

Calb et al., Structure and Function of the *Pseudomonas putida* Integration Host Factor, Journal of Bacteriology, Nov. 1996, vol. 178, No. 21, p. 6319-6326.

Freundlich et al., The Role of Integration Host Factor in Gene Expression in *Escherichia coli*, Molecular Microbiology, vol. 6, No. 18, Sep. 1992, pp. 2557-2563.

Zhang, Min et al., Metabolic Engineering of a Pentose Metabolism Pathway in Ethanologenic *Zymomonas mobilis*, Science, 1995, vol. 267:240-243.

Kim, In Seop et al., Kinetic and Nuclear Magnetic Resonance Studies of Xylose Metabolism by Recombinant *Zymomonas moblis* ZM4(pZB5), Applied and Environmental Microbiology, 2000, vol. 66, No. 1, pp. 186-193.

Kamei, Ken-Ichiro et al., Cellular Biosensing System for Assessing Immunomodulating Effects on the Inducible Nitric Oxide Synthase (iNOS) Cascade, Biotechnology Letters, 2003, vol. 25:321-325.

Lawford, Hugh G. et al., The Ffect of Acetic Acid on Fuel Ethanol Production by *Zymomonas*, Applied Biochemistry and Biotechnology, 1993, vol. 39:687-699.

Friedman, David I., Integration Host Factor: A Protein for All Reasons, Cell, 1988, vol. 55:545-554.

Vandyk, Tina K. et al., Characterization of the *Escherichia coli* AaeAB Efflux Pump: A Metabolic Relief Valve?, Journal of Bacteriology, Nov. 2004, pp. 7196-7204, vol. 186, No. 21.

Supple, Shane, G., Isolation and Preliminary Characterization of a *Zymomonas mobilis* Mutant With an Altered Preference for Xylose and Glucose Utilization, Biotechnology Letters, 2000, pp. 157-164, vol. 22.

National Center for Biotechnology Information, NC_006526.2, Region 1446603 to 1448633, *Zymomonas mobilis*.

National Center for Biotechnology Information, YP_001764723.1, *Burkholderia cenocepacia*.

Database Accession No. Q5NM4, Fusaric Acid Resistance Protein Conserved Region.

U.S. Appl. No. 13/161,734, filed Jun. 16, 2011, Perry G. Caimi et al.

International Search Report Dated Mar. 19, 2012, International Application No. PCT/US2011/064580.

\* cited by examiner

Figure 3

```
SEQ ID NO:7   Bcemn03_1426   MSASSPASTPAGGPFAAWYAAFGDWARTDGAAWLYLFKALLAAFIATGVSMRLDLPAPKT
SEQ ID NO:2   Zmo1432        ------------------------------MLFNLRQAAFALNCYIAAMLGLYVSMRIGLERPFW
                                                           :    : ::. :**::. ****:.* *

Bcemn03_1426   AMTTVFIVMQPQSGAVLAKSFYRVAGTIFGLIATLTFVGLFPQQPQLFLLAVALWVALCT
              Zmo1432        AMTTVYIVSHPLTGAIRSKSFYRVIGSFLGATFVLAVVPKFDNAPLFLCMILGLWASFCI
                             *****:** :*.:**: :****** *:::*   .*:.*  * : * :: : :.**.::*

Bcemn03_1426   AGAARNRNFRSYGFLLAGYTTALIGLPASQHPDGAFMSAMTRVAEIMVGIVSAGVVSALV
              Zmo1432        FIVVLDRSPRSYIFFLGIVTASVIGFLSVENPINVFHIASLRLQEICFGVVSAGFVHSVL
                             .. :*. *** *:*. *:::**: : ::* ..*  * *:.** .*:****.* :::

Bcemn03_1426   FPQTTGEQMRTTVRKRFGSFVDYVAAALSGQLDRAHIETIHTRFVADVVGFEAARSMAVF
              Zmo1432        FPHSVSNLLSRQLDQILHDCERWANHALAGDMTDIDAKDRQN-LTVDLTNVHFLGTHIPY
                             **::..: :    :  :   .:   **:*::   .:   :. :..*:....  :    :

Bcemn03_1426   EDPDTRMRSGRLARLNSEFMSASSRFHALHQLMNRLHAAGAQAAIDAIEPYFREIAPLLL
              Zmo1432        DTAGLRPTRMALAAVQDQIILLMPVIAAMEDRTREIDDAGGMS--EEITAYVESVRQWVA
                             :  .. *    **  ::.:::  . : *:.: ..:. **. :  * * .*...:  :

Bcemn03_1426   TPAGEPVRTSADAGHAAAQLLAWRDALPRRIRATRAALETQPDFP-LLDFDTAAELLYRF
              Zmo1432        DP---PVDDAAEASRLIARGNALGEKLKVENWRELLELNMIGRLRHLIEALQSTRLLVEA
                              *   **  *:*:*.:  *: *  : *  .    *:   : *::   ::.**  .

Bcemn03_1426   ITDLHEYAATYASLSSATHERERWIERYEPRTNATAMVIAAIRTATVILVLGWFWIETAW
              Zmo1432        VSHPEDHPPAMIAALSSAHRVRSMHRDYG------MAALTALSLFMVIMASSIFWIMTSW
                             ::. .::..:  : *::*. .  .*   .::*:   **::. *** *:*

Bcemn03_1426   PSGVTLTLTAAATCALASSTPRPTAMSAQMGMGTALAVCTGFLLTFGIYPHIDGFPLLCV
              Zmo1432        PNGSTGCLLAAMSFGLSAQAGDPVKQQGHYLLGAVIGVIVAGFYVFAIMTQIHEFELVML
                             *.* * * ** :.*::.:   *. ..: :*:.:.*  .. .*.* .:*. ** *:

Bcemn03_1426   ALAPLLAIGIFMTLKPKLAGYCMGYLIFFSFLAGPDNITHYDPTCFMNDSLALVLSMLAS
              Zmo1432        TMFPVLFIIGYLTADQNYLPIVRPFMVVFNLTMAIHPAYSADFELYFNNGLAIITGCGIS
                             :: *:* * ::*  .:  :::.*.: ..  *  ::*::.**::.     *

Bcemn03_1426   AIAFAVLFPPTAPWLKKRLFA----DLRHQAVAAGHARLAGLRTRFESGARDLMYQAHTL
              Zmo1432        LVGFKVMPRVIGADVMVRRLLQSGWRDLSATLKRPGAPDIVDWSSRMLDRIGLMAPRVSAT
                             :.* *:   * : :**:    **       .*   .: .   :*:       :  :.:

Bcemn03_1426   SADQPDVQRDALRWMFAVLETGNATIDLRHELAMLPSDPRYAPAMPWRRAIETMRSALSA
              Zmo1432        GTDQNVIRDDGIR----DLRIGICMLRLPQLAARVDEN---------VRHQISTLAQAIAG
                             .:** ::  :.*      *. *   **:  * : :          *: *.*: .*::.

Bcemn03_1426   LFTRPSAARFDATLAATNAAIDATRQTLDAFEPSREERHRLQRILSHLHFVRTALLDPES
              Zmo1432        YYDELSRS---PNAESSDIILTDIDRVIDSFVDLHNSIDPREGLTALVSLRRNMFPDAPG
                             :.*  ..   . .*::*. :  :.:*:* .:: :::   * : : *. :   *. :

Bcemn03_1426   PLEPLNRNRPVRPQPGASS
              Zmo1432        FIKQRSPA-----------
```

Figure 4

```
SEQ ID NO:2   zmo1432   ---MLFNLRQAAFALNCYIAAMLGLYVSMRIGLERPFWAMTTVYIVSH---------PLT
SEQ ID NO:8   EcaaeB    MGIFSIANQHIREAVKLATAIVLALFVGFHFQLETPRWAVLTAAIVAAGPAFAAGGEPYS
                         :  :   ::   **::   * :*.*:*.:::  ** * **: *. **:        * :

zmo1432   GAIRSKSFYRVIGSFLGATFVLAVVPKFDNAPLFLCMILGLWASFCIFIVVLDRSPRSYI
              EcaaeB    GAIRYRGFLRIIGTFIGCIAGLVIIIAMIRAPLLMILVCCIWAGFCTWISSLVRIENSYA
                        ****  :.* *:**:*:*.   *.::  : .***:: ::  :**.** :*   *  .**

zmo1432   FFLGIVTASVIGFLSVENPINVFHIASLRLQEICFGVVSAGFVHSVLFPHSVSNLLSRQL
              EcaaeB    WGLAGYTALIIVITIQPEPLLTPQFAVERCSEIVIGIVCAIMADLLFSPRSIKQEVDPEL
                        : *.  ** :*    :   :*: . ::*  * .**  *:*:*.*  :..  :: *:*:.:  :.*:* zmo1432   DQILHDCERWANHALAGDMTDIDAKDRQNLTVDLTNVHFLGTHIPYDTAGLRPTFMALAA
              EcaaeB    ESLLVAQYQLMQLCIKHGDGEVVDKAWGDLVRRTTALQGMRSNLNMESSRWARANRRLKA
                        :.:*    : :  : ..  ::  *   :*.   * :: :::  :::    :.   * * zmo1432   VQDQIILLMPVIAAMEDRTREIDDAGGMSEEITAYVESVRQWVADPPVDDAAEASRLIAR
              EcaaeB    IN--TLSLTLITQSCETYLIQNTRFELITDTFREFFD---------TPVETAQDVHKQLKR
                        ::  :  * :  : *   :        ::: :.:            .**: *  :. : : * zmo1432   GNALGEKLKVENWRELLELNMIGRLRELIEALQSTRLLVEAVSHPEDHPPAMIAALSSAH
              EcaaeB    ------LRRVIAWTGERETPVT--IYSWVAAATRYQLLKRGVISNTKINATEEEILQGEP
                              :*  *   * :  : * :** ..*  . .: *..

zmo1432   RVRSMHRDYGMAALTALTLFMVIMASSIFWIMTSWPNGSTGCLLAAMSFGLSAQAGDPVK
              EcaaeB    EVKVESAERRHAMVNFWRTTLSCILGTLFWLWTGWTSCSGAMVMIAVVTSLAMRLPNPRM
                        .*:   :   * :.    : :.::**:*.*..**  . :: *:  .*:  .:   :* zmo1432   QQGHYLLGAVIGVIVAGFYVFAIMTQIHEFELVMLTMFPVLFIIGYLTADQNYLPIVRPF
              EcaaeB    VAIDFIYGTIAALPLGLLYFLVIIPNTQQSMLLLCISIAVLGFFLGIEVQKRRLGSMGAL
                          .::  *:: .: :. :*.:.:*:.:  *::   *:: :.** ::.  .*   * .: * zmo1432   MVVFNLTMAIHPAYSADFELYFNNGLAIITGCGISLVGFKVMRVIGADVMVRRLLQSGWR
              EcaaeB    ASTINIIVLDNP-MTFHFSQFLDSALGQIVGCVLAFTVILLVRDKSRDRTGRVLLNQFVS
                        . :*: :  ::* : .*. :::..*. *. *:*  ::: .  : ::*  *   * **:.

zmo1432   DLSATLKRPGAPDIVDWSSRMLDRIGLMAPRVSATGTDQNVIRDDGIRDLRIGICMLRLR
              EcaaeB    AAVSAMTTNVARRKENHLPALYQQLFLLMNKFPG-----------DLPKFRLALTMIIAH
                         ::. * :   . .: :::  *:  :...     .:  ..*:..: *: :

zmo1432   QLAARVDENVRRQISTLAQAIAGYYDELSRSPNAESSDIILTDIDRVIDSFVDLHNSIDR
              EcaaeB    QRLRDAPIPVNEDLSAFHRQMRRTADEVISARSDDKRRRYFGQLLEELEIYQEKLRIWQA
                        *    ,   *..::*::  :  * *.:  :  :. . :   ::  :: :: :  :

zmo1432   REGLTALVSIRRNMFPDAPGFIKQRSPA
              EcaaeB      PPQVTEPVHRLAGMLHKYQHALTDS---
                         :*  *   .*:  .   ::.:
```

SEQUENCE LISTING

<160> NUMBER OF SEQ ID NOS: 12

<210> SEQ ID NO 1
<211> LENGTH: 2031
<212> TYPE: DNA
<213> ORGANISM: Zymomonas mobilis

<400> SEQUENCE: 1
atgctgttta atttacggca ggcagctttt gcgcttaatt gttatatagc tgcaatgctc     60
ggcctctatg tctctatgcg gattgggctt gaacgtcctt tctgggcgat gacgactgtc    120

| | |
|---|---|
| tatatcgtta gtcatcccct tacggggct atacgttcta atccttttta tcgcgtcatt | 180 |
| ggttccttcc ttggcgctac ttttgttctg gccgttgtcc caaaatttga taatgcgccc | 240 |
| ctttttctct gtatgatttt agggctgtgg gcgtcttttt gtatttttat tgttgttctc | 300 |
| gaccgttcac cgcgctctta tattttcttt cttggtatcg ttacggcctc tgttatcggc | 360 |
| tttcttagcg tagaaaaccc tatcaatgtt ttccatatag cctctcttcg acttcaggaa | 420 |
| atctgctttg gggttgtatc ggcaggcttt gttcattccg tgcttttttcc ccattccgtc | 480 |
| agtaatcttt tatcgcgtca attggatcag attctccatg attgcgaacg ctgggctaac | 540 |
| catgccttgg ccggagatat gacggatatt gatgcgaaag accgccaaaa tctgaccgtt | 600 |
| gaccttacca atgtccattt tcttgggaca catatcccct atgacacagc gggattgcgg | 660 |
| ccaacgcgta tggctttagc cgcggttcag gatcagatta ttcttttgat gcctgttatc | 720 |
| gccgctatgg aagatcggac aagagaaatt gacgatgccg gcggtatgtc ggaagagatt | 780 |
| accgcctatg tcgaatctgt tcggcaatgg gtcgcagatc ccccgttga tgatgcggca | 840 |
| gaagccagtc gtttgattgc gcgcggcaat gccttgggtg aaaaactaaa ggttgaaaat | 900 |
| tggcgcgaac tgctcgagct aaatatgatc gggcgactgc gtcatttgat cgaagccttg | 960 |
| caatcgaccc gtttgttggt cgaagccgtc agccatccag aagatcatcc acctgccatg | 1020 |
| attgccgctt taagtagcgc ccatcgcgtt cgctcaatgc atcgcgacta tggtatggcg | 1080 |
| gctttaaccg ctttgacatt gttatggtc attatggcct catccatttt ctggatcatg | 1140 |
| accagttggc caaatggttc gaccggttgc cttttggcgg cgatgtcgtt cggtctgtcg | 1200 |
| gcccaggcag gtgaccctgt aaacaacaa gggcattatc tcctcggggc tgtcatcggg | 1260 |
| gtgattgtcg ctggttttta tgtgtttgcc atcatgacac aaattcatga atttgaattg | 1320 |
| gtcatgctga cgatgttccc tgtgctgttc attatcggct atcttactgc cgatcagaac | 1380 |
| tacctgccga ttgttcgacc ctttatggtt gtcttcaacc taacaatggc aatccatccc | 1440 |
| gcttattctg ccgatttcga gctttatttt aacaatggtt tggccattat taccggctgc | 1500 |
| ggcatctccc ttgtcggttt caaagtaatg cgcgttatcg gtgccgatgt gatggtcaga | 1560 |
| aggcttctgc aatctgggtg gcgtgatctt tcggcaacct aaaaacgacc gggcgcgccc | 1620 |
| gatatcgttg attggtcaag ccgtatgctc gatcgtatcg gtcttatggc accgcgcgtt | 1680 |
| tcagcaacag ggacagatca gaatgttatc cgcgatgatg gtattcgcga tttgcgtatc | 1740 |
| ggtatctgta tgctgcgctt gcggcagctg gctgctcgtg ttgatgaaaa tgtccgtcat | 1800 |
| caaatatcca cttggcgca agccattgct ggctattatg acgaattgtc acggtcaccg | 1860 |
| aatgctgaat cttcggatat catttgaca gatatcgatc gtgttattga tagctttgtg | 1920 |
| gatctacata attcaatcga tcgccgcgaa gggctgaccg ccttggtcag cttacgtcgc | 1980 |
| aatatgtttc ctgatgcacc agggttcata aacaacgaa gtccggcatg a | 2031 |

<210> SEQ ID NO 2
<211> LENGTH: 676
<212> TYPE: PRT
<213> ORGANISM: Zymomonas mobilis

<400> SEQUENCE: 2

Met Leu Phe Asn Leu Arg Gln Ala Ala Phe Ala Leu Asn Cys Tyr Ile
1               5                   10                  15

Ala Ala Met Leu Gly Leu Tyr Val Ser Met Arg Ile Gly Leu Glu Arg
                20                  25                  30

Pro Phe Trp Ala Met Thr Thr Val Tyr Ile Val Ser His Pro Leu Thr
        35                  40                  45

```
Gly Ala Ile Arg Ser Lys Ser Phe Tyr Arg Val Ile Gly Ser Phe Leu
         50                  55                  60
Gly Ala Thr Phe Val Leu Ala Val Val Pro Lys Phe Asp Asn Ala Pro
 65                  70                  75                  80
Leu Phe Leu Cys Met Ile Leu Gly Leu Trp Ala Ser Phe Cys Ile Phe
                     85                  90                  95
Ile Val Val Leu Asp Arg Ser Pro Arg Ser Tyr Ile Phe Phe Leu Gly
                    100                 105                 110
Ile Val Thr Ala Ser Val Ile Gly Phe Leu Ser Val Glu Asn Pro Ile
                115                 120                 125
Asn Val Phe His Ile Ala Ser Leu Arg Leu Gln Glu Ile Cys Phe Gly
            130                 135                 140
Val Val Ser Ala Gly Phe Val His Ser Val Leu Phe Pro His Ser Val
145                 150                 155                 160
Ser Asn Leu Leu Ser Arg Gln Leu Asp Gln Ile Leu His Asp Cys Glu
                    165                 170                 175
Arg Trp Ala Asn His Ala Leu Ala Gly Asp Met Thr Asp Ile Asp Ala
                180                 185                 190
Lys Asp Arg Gln Asn Leu Thr Val Asp Leu Thr Asn Val His Phe Leu
            195                 200                 205
Gly Thr His Ile Pro Tyr Asp Thr Ala Gly Leu Arg Pro Thr Arg Met
210                 215                 220
Ala Leu Ala Ala Val Gln Asp Gln Ile Ile Leu Leu Met Pro Val Ile
225                 230                 235                 240
Ala Ala Met Glu Asp Arg Thr Arg Glu Ile Asp Ala Gly Gly Met
                245                 250                 255
Ser Glu Glu Ile Thr Ala Tyr Val Glu Ser Val Arg Gln Trp Val Ala
                260                 265                 270
Asp Pro Pro Val Asp Asp Ala Ala Glu Ala Ser Arg Leu Ile Ala Arg
            275                 280                 285
Gly Asn Ala Leu Gly Glu Lys Leu Lys Val Glu Asn Trp Arg Glu Leu
290                 295                 300
Leu Glu Leu Asn Met Ile Gly Arg Leu Arg His Leu Ile Glu Ala Leu
305                 310                 315                 320
Gln Ser Thr Arg Leu Leu Val Glu Ala Val Ser His Pro Glu Asp His
                325                 330                 335
Pro Pro Ala Met Ile Ala Ala Leu Ser Ser Ala His Arg Val Arg Ser
                340                 345                 350
Met His Arg Asp Tyr Gly Met Ala Leu Thr Ala Leu Thr Leu Phe
            355                 360                 365
Met Val Ile Met Ala Ser Ser Ile Phe Trp Ile Met Thr Ser Trp Pro
370                 375                 380
Asn Gly Ser Thr Gly Cys Leu Leu Ala Ala Met Ser Phe Gly Leu Ser
385                 390                 395                 400
Ala Gln Ala Gly Asp Pro Val Lys Gln Gln Gly His Tyr Leu Leu Gly
                    405                 410                 415
Ala Val Ile Gly Val Ile Val Ala Gly Phe Tyr Val Phe Ala Ile Met
                420                 425                 430
Thr Gln Ile His Glu Phe Glu Leu Val Met Leu Thr Met Phe Pro Val
            435                 440                 445
Leu Phe Ile Ile Gly Tyr Leu Thr Ala Asp Gln Asn Tyr Leu Pro Ile
450                 455                 460
Val Arg Pro Phe Met Val Val Phe Asn Leu Thr Met Ala Ile His Pro
465                 470                 475                 480
```

-continued

```
Ala Tyr Ser Ala Asp Phe Glu Leu Tyr Phe Asn Asn Gly Leu Ala Ile
                485                 490                 495

Ile Thr Gly Cys Gly Ile Ser Leu Val Gly Phe Lys Val Met Arg Val
            500                 505                 510

Ile Gly Ala Asp Val Met Val Arg Arg Leu Leu Gln Ser Gly Trp Arg
        515                 520                 525

Asp Leu Ser Ala Thr Leu Lys Arg Pro Gly Ala Pro Asp Ile Val Asp
    530                 535                 540

Trp Ser Ser Arg Met Leu Asp Arg Ile Gly Leu Met Ala Pro Arg Val
545                 550                 555                 560

Ser Ala Thr Gly Thr Asp Gln Asn Val Ile Arg Asp Asp Gly Ile Arg
                565                 570                 575

Asp Leu Arg Ile Gly Ile Cys Met Leu Arg Leu Arg Gln Leu Ala Ala
            580                 585                 590

Arg Val Asp Glu Asn Val Arg His Gln Ile Ser Thr Leu Ala Gln Ala
        595                 600                 605

Ile Ala Gly Tyr Tyr Asp Glu Leu Ser Arg Ser Pro Asn Ala Glu Ser
    610                 615                 620

Ser Asp Ile Ile Leu Thr Asp Ile Asp Arg Val Ile Asp Ser Phe Val
625                 630                 635                 640

Asp Leu His Asn Ser Ile Asp Arg Arg Glu Gly Leu Thr Ala Leu Val
                645                 650                 655

Ser Leu Arg Arg Asn Met Phe Pro Asp Ala Pro Gly Phe Ile Lys Gln
            660                 665                 670

Arg Ser Pro Ala
        675

<210> SEQ ID NO 3
<211> LENGTH: 676
<212> TYPE: PRT
<213> ORGANISM: artificial sequence
<220> FEATURE:
<223> OTHER INFORMATION: mutant zmo1432 encoded protein - at position
      #366

<400> SEQUENCE: 3

Met Leu Phe Asn Leu Arg Gln Ala Ala Phe Ala Leu Asn Cys Tyr Ile
1               5                   10                  15

Ala Ala Met Leu Gly Leu Tyr Val Ser Met Arg Ile Gly Leu Glu Arg
                20                  25                  30

Pro Phe Trp Ala Met Thr Thr Val Tyr Ile Val Ser His Pro Leu Thr
            35                  40                  45

Gly Ala Ile Arg Ser Lys Ser Phe Tyr Arg Val Ile Gly Ser Phe Leu
        50                  55                  60

Gly Ala Thr Phe Val Leu Ala Val Val Pro Lys Phe Asp Asn Ala Pro
65                  70                  75                  80

Leu Phe Leu Cys Met Ile Leu Gly Leu Trp Ala Ser Phe Cys Ile Phe
                85                  90                  95

Ile Val Val Leu Asp Arg Ser Pro Arg Ser Tyr Ile Phe Phe Leu Gly
            100                 105                 110

Ile Val Thr Ala Ser Val Ile Gly Phe Leu Ser Val Glu Asn Pro Ile
        115                 120                 125

Asn Val Phe His Ile Ala Ser Leu Arg Leu Gln Glu Ile Cys Phe Gly
    130                 135                 140

Val Val Ser Ala Gly Phe Val His Ser Val Leu Phe Pro His Ser Val
145                 150                 155                 160
```

-continued

```
Ser Asn Leu Leu Ser Arg Gln Leu Asp Gln Ile Leu His Asp Cys Glu
            165                 170                 175

Arg Trp Ala Asn His Ala Leu Ala Gly Asp Met Thr Asp Ile Asp Ala
        180                 185                 190

Lys Asp Arg Gln Asn Leu Thr Val Asp Leu Thr Asn Val His Phe Leu
        195                 200                 205

Gly Thr His Ile Pro Tyr Asp Thr Ala Gly Leu Arg Pro Thr Arg Met
        210                 215                 220

Ala Leu Ala Ala Val Gln Asp Gln Ile Ile Leu Leu Met Pro Val Ile
225                 230                 235                 240

Ala Ala Met Glu Asp Arg Thr Arg Glu Ile Asp Asp Ala Gly Gly Met
            245                 250                 255

Ser Glu Glu Ile Thr Ala Tyr Val Glu Ser Val Arg Gln Trp Val Ala
            260                 265                 270

Asp Pro Pro Val Asp Asp Ala Ala Glu Ala Ser Arg Leu Ile Ala Arg
            275                 280                 285

Gly Asn Ala Leu Gly Glu Lys Leu Lys Val Glu Asn Trp Arg Glu Leu
        290                 295                 300

Leu Glu Leu Asn Met Ile Gly Arg Leu Arg His Leu Ile Glu Ala Leu
305                 310                 315                 320

Gln Ser Thr Arg Leu Leu Val Glu Ala Val Ser His Pro Glu Asp His
            325                 330                 335

Pro Pro Ala Met Ile Ala Ala Leu Ser Ser Ala His Arg Val Arg Ser
            340                 345                 350

Met His Arg Asp Tyr Gly Met Ala Ala Leu Thr Ala Leu Arg Leu Phe
        355                 360                 365

Met Val Ile Met Ala Ser Ser Ile Phe Trp Ile Met Thr Ser Trp Pro
        370                 375                 380

Asn Gly Ser Thr Gly Cys Leu Leu Ala Ala Met Ser Phe Gly Leu Ser
385                 390                 395                 400

Ala Gln Ala Gly Asp Pro Val Lys Gln Gln Gly His Tyr Leu Leu Gly
            405                 410                 415

Ala Val Ile Gly Val Ile Val Ala Gly Phe Tyr Val Phe Ala Ile Met
            420                 425                 430

Thr Gln Ile His Glu Phe Glu Leu Val Met Leu Thr Met Phe Pro Val
        435                 440                 445

Leu Phe Ile Ile Gly Tyr Leu Thr Ala Asp Gln Asn Tyr Leu Pro Ile
        450                 455                 460

Val Arg Pro Phe Met Val Phe Asn Leu Thr Met Ala Ile His Pro
465                 470                 475                 480

Ala Tyr Ser Ala Asp Phe Glu Leu Tyr Phe Asn Asn Gly Leu Ala Ile
            485                 490                 495

Ile Thr Gly Cys Gly Ile Ser Leu Val Gly Phe Lys Val Met Arg Val
            500                 505                 510

Ile Gly Ala Asp Val Met Val Arg Leu Leu Gln Ser Gly Trp Arg
        515                 520                 525

Asp Leu Ser Ala Thr Leu Lys Arg Pro Gly Ala Pro Asp Ile Val Asp
        530                 535                 540

Trp Ser Ser Arg Met Leu Asp Arg Ile Gly Leu Met Ala Pro Arg Val
545                 550                 555                 560

Ser Ala Thr Gly Thr Asp Gln Asn Val Ile Arg Asp Gly Ile Arg
            565                 570                 575

Asp Leu Arg Ile Gly Ile Cys Met Leu Arg Leu Arg Gln Leu Ala Ala
            580                 585                 590
```

-continued

```
Arg Val Asp Glu Asn Val Arg His Gln Ile Ser Thr Leu Ala Gln Ala
    595                 600                 605

Ile Ala Gly Tyr Tyr Asp Glu Leu Ser Arg Ser Pro Asn Ala Glu Ser
    610                 615                 620

Ser Asp Ile Ile Leu Thr Asp Ile Asp Arg Val Ile Asp Ser Phe Val
625                 630                 635                 640

Asp Leu His Asn Ser Ile Asp Arg Arg Glu Gly Leu Thr Ala Leu Val
                645                 650                 655

Ser Leu Arg Arg Asn Met Phe Pro Asp Ala Pro Gly Phe Ile Lys Gln
            660                 665                 670

Arg Ser Pro Ala
            675

<210> SEQ ID NO 4
<211> LENGTH: 676
<212> TYPE: PRT
<213> ORGANISM: artificial sequence
<220> FEATURE:
<223> OTHER INFORMATION: zmo1432 encoded protein with #117 mutation

<400> SEQUENCE: 4

Met Leu Phe Asn Leu Arg Gln Ala Ala Phe Ala Leu Asn Cys Tyr Ile
1               5                   10                  15

Ala Ala Met Leu Gly Leu Tyr Val Ser Met Arg Ile Gly Leu Glu Arg
            20                  25                  30

Pro Phe Trp Ala Met Thr Thr Val Tyr Ile Val Ser His Pro Leu Thr
        35                  40                  45

Gly Ala Ile Arg Ser Lys Ser Phe Tyr Arg Val Ile Gly Ser Phe Leu
    50                  55                  60

Gly Ala Thr Phe Val Leu Ala Val Val Pro Lys Phe Asp Asn Ala Pro
65                  70                  75                  80

Leu Phe Leu Cys Met Ile Leu Gly Leu Trp Ala Ser Phe Cys Ile Phe
                85                  90                  95

Ile Val Val Leu Asp Arg Ser Pro Arg Ser Tyr Ile Phe Phe Leu Gly
            100                 105                 110

Ile Val Thr Ala Phe Val Ile Gly Phe Leu Ser Val Glu Asn Pro Ile
        115                 120                 125

Asn Val Phe His Ile Ala Ser Leu Arg Leu Gln Glu Ile Cys Phe Gly
    130                 135                 140

Val Val Ser Ala Gly Phe Val His Ser Val Leu Phe Pro His Ser Val
145                 150                 155                 160

Ser Asn Leu Leu Ser Arg Gln Leu Asp Gln Ile Leu His Asp Cys Glu
                165                 170                 175

Arg Trp Ala Asn His Ala Leu Ala Gly Asp Met Thr Asp Ile Asp Ala
            180                 185                 190

Lys Asp Arg Gln Asn Leu Thr Val Asp Leu Thr Asn Val His Phe Leu
        195                 200                 205

Gly Thr His Ile Pro Tyr Asp Thr Ala Gly Leu Arg Pro Thr Arg Met
    210                 215                 220

Ala Leu Ala Ala Val Gln Asp Gln Ile Ile Leu Leu Met Pro Val Ile
225                 230                 235                 240

Ala Ala Met Glu Asp Arg Thr Arg Glu Ile Asp Asp Ala Gly Gly Met
                245                 250                 255

Ser Glu Glu Ile Thr Ala Tyr Val Glu Ser Val Arg Gln Trp Val Ala
            260                 265                 270
```

```
Asp Pro Pro Val Asp Asp Ala Ala Glu Ala Ser Arg Leu Ile Ala Arg
        275                 280                 285

Gly Asn Ala Leu Gly Glu Lys Leu Lys Val Glu Asn Trp Arg Glu Leu
290                 295                 300

Leu Glu Leu Asn Met Ile Gly Arg Leu Arg His Leu Ile Glu Ala Leu
305                 310                 315                 320

Gln Ser Thr Arg Leu Leu Val Glu Ala Val Ser His Pro Glu Asp His
                325                 330                 335

Pro Pro Ala Met Ile Ala Ala Leu Ser Ser Ala His Arg Val Arg Ser
                340                 345                 350

Met His Arg Asp Tyr Gly Met Ala Ala Leu Thr Ala Leu Thr Leu Phe
            355                 360                 365

Met Val Ile Met Ala Ser Ser Ile Phe Trp Ile Met Thr Ser Trp Pro
    370                 375                 380

Asn Gly Ser Thr Gly Cys Leu Leu Ala Ala Met Ser Phe Gly Leu Ser
385                 390                 395                 400

Ala Gln Ala Gly Asp Pro Val Lys Gln Gln Gly His Tyr Leu Leu Gly
                405                 410                 415

Ala Val Ile Gly Val Ile Val Ala Gly Phe Tyr Val Phe Ala Ile Met
            420                 425                 430

Thr Gln Ile His Glu Phe Glu Leu Val Met Leu Thr Met Phe Pro Val
        435                 440                 445

Leu Phe Ile Ile Gly Tyr Leu Thr Ala Asp Gln Asn Tyr Leu Pro Ile
    450                 455                 460

Val Arg Pro Phe Met Val Val Phe Asn Leu Thr Met Ala Ile His Pro
465                 470                 475                 480

Ala Tyr Ser Ala Asp Phe Glu Leu Tyr Phe Asn Asn Gly Leu Ala Ile
                485                 490                 495

Ile Thr Gly Cys Gly Ile Ser Leu Val Gly Phe Lys Val Met Arg Val
            500                 505                 510

Ile Gly Ala Asp Val Met Val Arg Arg Leu Leu Gln Ser Gly Trp Arg
        515                 520                 525

Asp Leu Ser Ala Thr Leu Lys Arg Pro Gly Ala Pro Asp Ile Val Asp
    530                 535                 540

Trp Ser Ser Arg Met Leu Asp Arg Ile Gly Leu Met Ala Pro Arg Val
545                 550                 555                 560

Ser Ala Thr Gly Thr Asp Gln Asn Val Ile Arg Asp Asp Gly Ile Arg
                565                 570                 575

Asp Leu Arg Ile Gly Ile Cys Met Leu Arg Leu Arg Gln Leu Ala Ala
            580                 585                 590

Arg Val Asp Glu Asn Val Arg His Gln Ile Ser Thr Leu Ala Gln Ala
        595                 600                 605

Ile Ala Gly Tyr Tyr Asp Glu Leu Ser Arg Ser Pro Asn Ala Glu Ser
    610                 615                 620

Ser Asp Ile Ile Leu Thr Asp Ile Asp Arg Val Ile Asp Ser Phe Val
625                 630                 635                 640

Asp Leu His Asn Ser Ile Asp Arg Arg Glu Gly Leu Thr Ala Leu Val
                645                 650                 655

Ser Leu Arg Arg Asn Met Phe Pro Asp Ala Pro Gly Phe Ile Lys Gln
            660                 665                 670

Arg Ser Pro Ala
        675
```

```
<210> SEQ ID NO 5
<211> LENGTH: 346
<212> TYPE: PRT
<213> ORGANISM: Burkholderia cepacia

<400> SEQUENCE: 5

Met Ser Ala Met Thr Arg Val Ser Glu Val Ile Ile Gly Ile Val Ser
 1               5                  10                  15

Ala Gly Val Val Ser Ala Leu Val Phe Pro Arg Tyr Thr Gly Glu Gln
            20                  25                  30

Met Arg Thr Thr Val Arg Lys Arg Phe Gly Ser Phe Val Asp Tyr Val
        35                  40                  45

Ala Ser Ala Leu Ser Gly Gln Leu Asp Arg Ala His Ile Glu Thr Ile
    50                  55                  60

His Thr Arg Phe Ala Tyr Val Val Gly Phe Glu Ala Ala Arg Ser Met
65                  70                  75                  80

Ala Val Phe Glu Asp Pro Asp Thr Arg Met Arg Ser Gly Arg Leu Ala
                85                  90                  95

Arg Leu Asn Ser Glu Phe Met Ser Ala Ser Ser Arg Phe His Ala Leu
            100                 105                 110

His Gln Leu Met Asn Arg Leu His Ala Ala Gly Ala Gln Ala Ala Ile
        115                 120                 125

Asp Ala Ile Glu Pro Tyr Phe Arg Glu Ile Ala Pro Leu Leu Thr Arg
    130                 135                 140

Asn Gly Glu Pro Val Arg Thr Ser Ile Asp Ala Ala His Ser Ala Glu
145                 150                 155                 160

Gln Leu Leu Ala Trp Arg Asp Ala Leu Pro Arg Arg Ile Arg Ala Thr
                165                 170                 175

Arg Ala Glu Leu Glu Thr Gln Pro Asp Phe Pro Leu Leu Asp Phe Asp
            180                 185                 190

Thr Ala Ala Glu Leu Leu Tyr Arg Phe Ile Thr Asp Leu Gln Glu Tyr
        195                 200                 205

Ala Ala Thr Tyr Ala Ser Leu Ala Thr Ala Thr His Glu Arg Glu Arg
    210                 215                 220

Trp Ile Glu Arg Tyr Glu Pro Arg Thr Asn Lys Thr Ala Ala Thr Ile
225                 230                 235                 240

Ala Gly Ile Arg Thr Ala Thr Val Ile Leu Ala Leu Gly Trp Phe Trp
                245                 250                 255

Ile Glu Thr Ala Trp Pro Ser Gly Val Met Leu Val Leu Asn Ala Ala
            260                 265                 270

Ala Thr Cys Ala Leu Ala Ser Ser Ala Pro Arg Pro Thr Ala Met Ala
        275                 280                 285

Ala Gln Met Gly Met Gly Thr Ala Leu Ala Val Cys Thr Gly Phe Leu
    290                 295                 300

Leu Thr Phe Gly Ile Tyr Pro Arg Ile Asp Gly Phe Val Leu Leu Cys
305                 310                 315                 320

Ala Ala Leu Ala Pro Leu Leu Ala Ile Gly Ile Tyr Met Ser Leu Lys
                325                 330                 335

Pro Lys Leu Ala Gly Tyr Gly Gly Ala Ile
            340                 345

<210> SEQ ID NO 6
<211> LENGTH: 234
<212> TYPE: PRT
<213> ORGANISM: Klebsiella oxytoca
```

```
<400> SEQUENCE: 6

Met Arg Arg Gln Asp Thr Phe Ser Ile Ala Ile Pro Ser Ser Ala Ala
1               5                   10                  15

Arg Thr Ala Leu Gly Ala Phe Val Ile Leu Ser Gly Cys Leu Leu
            20                  25                  30

Trp Ile Tyr Ser Ala Trp Pro Asp Gly Gly Thr Ala Val Ser Ile Leu
            35                  40                  45

Gly Val Cys Cys Thr Leu Phe Gly Ser Phe Asp Thr Pro Ala Pro His
    50                  55                  60

Ile Val Lys Tyr Ile Ile Gly Ser Val Trp Gly Val Ile Ser Leu
65                  70                  75                  80

Ile Tyr Ser Phe Ala Leu Leu Pro Pro Leu Ser Asp Phe Pro Val Leu
                85                  90                  95

Val Ala Val Leu Ala Pro Val Tyr Leu Leu Ala Gly Ser Leu Gln Ala
            100                 105                 110

Arg Pro Pro Thr Thr Phe Met Ala Met Gly Ile Thr Leu Thr Leu Pro
            115                 120                 125

Val Leu Cys Glu Leu Gly Ala Arg Tyr Ser Gly Asp Phe Ala Asp Ala
130                 135                 140

Ala Asn Thr Ala Ile Ala Leu Phe Phe Ala Thr Gly Phe Ala Val Ile
145                 150                 155                 160

Gly Met Ser Leu Leu Gln Thr Val Gln Ala Asp Ala Ile Lys Arg
                165                 170                 175

Leu Leu Lys Leu Cys Gln Arg Asp Ile Arg Arg Ser Val Ser Gly Val
            180                 185                 190

Phe Lys Gly Asp Glu Thr His Trp Thr Asn Leu Met Ile Asp Arg Gly
            195                 200                 205

Ala Leu Leu Leu Pro Arg Leu Arg Ala Ala Gly Ser Pro Pro Pro Gly
        210                 215                 220

Arg Ser Ile Ala Trp Cys Thr Phe Cys Ala
225                 230

<210> SEQ ID NO 7
<211> LENGTH: 734
<212> TYPE: PRT
<213> ORGANISM: Burkholderia cepacia

<400> SEQUENCE: 7

Met Ser Ala Ser Ser Pro Ala Ser Thr Pro Ala Gly Gly Pro Phe Ala
1               5                   10                  15

Ala Trp Tyr Ala Ala Phe Gly Asp Trp Ala Arg Thr Asp Gly Ala Ala
            20                  25                  30

Trp Leu Tyr Leu Phe Lys Ala Leu Leu Ala Ala Phe Ile Ala Thr Gly
            35                  40                  45

Val Ser Met Arg Leu Asp Leu Pro Ala Pro Lys Thr Ala Met Thr Thr
    50                  55                  60

Val Phe Ile Val Met Gln Pro Gln Ser Gly Ala Val Leu Ala Lys Ser
65              70                  75                  80

Phe Tyr Arg Val Ala Gly Thr Ile Phe Gly Leu Ile Ala Thr Leu Thr
                85                  90                  95

Phe Val Gly Leu Phe Pro Gln Gln Pro Gln Leu Phe Leu Leu Ala Val
            100                 105                 110

Ala Leu Trp Val Ala Leu Cys Thr Ala Gly Ala Ala Arg Asn Arg Asn
            115                 120                 125
```

-continued

Phe Arg Ser Tyr Gly Phe Leu Leu Ala Gly Tyr Thr Thr Ala Leu Ile
130                 135                 140

Gly Leu Pro Ala Ser Gln His Pro Asp Gly Ala Phe Met Ser Ala Met
145                 150                 155                 160

Thr Arg Val Ala Glu Ile Met Val Gly Ile Val Ser Ala Gly Val Val
            165                 170                 175

Ser Ala Leu Val Phe Pro Arg Thr Thr Gly Glu Gln Met Arg Thr Thr
            180                 185                 190

Val Arg Lys Arg Phe Gly Ser Phe Val Asp Tyr Val Ala Ala Ala Leu
        195                 200                 205

Ser Gly Gln Leu Asp Arg Ala His Ile Glu Thr Ile His Thr Arg Phe
210                 215                 220

Val Ala Asp Val Val Gly Phe Glu Ala Ala Arg Ser Met Ala Val Phe
225                 230                 235                 240

Glu Asp Pro Asp Thr Arg Met Arg Ser Gly Arg Leu Ala Arg Leu Asn
                245                 250                 255

Ser Glu Phe Met Ser Ala Ser Ser Arg Phe His Ala Leu His Gln Leu
                260                 265                 270

Met Asn Arg Leu His Ala Gly Ala Gln Ala Ile Asp Ala Ile
            275                 280                 285

Glu Pro Tyr Phe Arg Glu Ile Ala Pro Leu Leu Leu Thr Pro Ala Gly
290                 295                 300

Glu Pro Val Arg Thr Ser Ala Asp Ala Gly His Ala Ala Thr Gln Leu
305                 310                 315                 320

Leu Ala Trp Arg Asp Ala Leu Pro Arg Arg Ile Arg Ala Thr Arg Ala
                325                 330                 335

Ala Leu Glu Thr Gln Pro Asp Phe Pro Leu Leu Asp Phe Asp Thr Ala
                340                 345                 350

Ala Glu Leu Leu Tyr Arg Phe Ile Thr Asp Leu His Glu Tyr Ala Ala
            355                 360                 365

Thr Tyr Ala Ser Leu Ser Ser Ala Thr His Glu Arg Glu Arg Trp Ile
370                 375                 380

Glu Arg Tyr Glu Pro Arg Thr Asn Ala Thr Ala Met Val Ile Ala Ala
385                 390                 395                 400

Ile Arg Thr Ala Thr Val Ile Leu Val Leu Gly Trp Phe Trp Ile Glu
                405                 410                 415

Thr Ala Trp Pro Ser Gly Val Thr Met Thr Leu Thr Ala Ala Ala Thr
                420                 425                 430

Cys Ala Leu Ala Ser Ser Thr Pro Arg Pro Thr Ala Met Ser Ala Gln
            435                 440                 445

Met Gly Met Gly Thr Ala Leu Ala Val Cys Thr Gly Phe Leu Leu Thr
450                 455                 460

Phe Gly Ile Tyr Pro His Ile Asp Gly Phe Pro Leu Leu Cys Val Ala
465                 470                 475                 480

Leu Ala Pro Leu Leu Ala Ile Gly Ile Phe Met Thr Leu Lys Pro Lys
                485                 490                 495

Leu Ala Gly Tyr Gly Met Gly Tyr Leu Ile Phe Phe Ser Phe Leu Ala
                500                 505                 510

Gly Pro Asp Asn Ile Thr His Tyr Asp Pro Thr Ser Phe Met Asn Asp
            515                 520                 525

Ser Leu Ala Leu Val Leu Ala Met Leu Ala Ser Ala Ile Ala Phe Ala
530                 535                 540

Val Leu Phe Pro Pro Thr Ala Pro Trp His Lys Lys Arg Leu Phe Ala
545                 550                 555                 560

-continued

```
Asp Leu Arg His Gln Ala Val Ala Ala Gly His Ala Arg Leu Ala Gly
                565                 570                 575

Leu Arg Thr Arg Phe Glu Ser Gly Ala Arg Asp Leu Met Tyr Gln Ala
            580                 585                 590

His Thr Leu Ser Ala Asp Gln Pro Asp Val Gln Arg Asp Ala Leu Arg
        595                 600                 605

Trp Met Phe Ala Val Leu Glu Thr Gly Asn Ala Thr Ile Asp Leu Arg
    610                 615                 620

His Glu Leu Ala Thr Leu Pro Ala Asp Pro Arg Tyr Ala Pro Ala Met
625                 630                 635                 640

Pro Trp Arg Arg Ala Ile Asp Thr Met Arg Thr Ala Leu Ser Ala Leu
                645                 650                 655

Phe Thr Arg Pro Ser Ala Ala Arg Phe Asp Ala Thr Leu Ala Ala Thr
            660                 665                 670

Asn Ala Ala Ile Asp Ala Thr Arg Gln Thr Leu Asp Ala Val Glu Pro
        675                 680                 685

Ser Arg Asp Glu Arg His Arg Leu Gln Arg Ile Leu Ser His Leu His
    690                 695                 700

Phe Val Arg Thr Ala Leu Leu Asp Pro Glu Ser Pro Leu Glu Pro Leu
705                 710                 715                 720

Asn Arg Asn Arg Pro Val His Pro Gln Pro Gly Ala Ser Ser
                725                 730

<210> SEQ ID NO 8
<211> LENGTH: 655
<212> TYPE: PRT
<213> ORGANISM: Escherichia coli

<400> SEQUENCE: 8

Met Gly Ile Phe Ser Ile Ala Asn Gln His Ile Arg Phe Ala Val Lys
1               5                   10                  15

Leu Ala Thr Ala Ile Val Leu Ala Leu Phe Val Gly Phe His Phe Gln
            20                  25                  30

Leu Glu Thr Pro Arg Trp Ala Val Leu Thr Ala Ala Ile Val Ala Ala
        35                  40                  45

Gly Thr Ala Phe Ala Ala Gly Gly Glu Pro Tyr Ser Gly Ala Ile Arg
    50                  55                  60

Tyr Arg Gly Phe Leu Arg Ile Ile Gly Thr Phe Ile Gly Cys Ile Ala
65                  70                  75                  80

Gly Leu Val Ile Ile Ile Ala Met Ile Arg Ala Pro Leu Leu Met Ile
                85                  90                  95

Leu Val Cys Cys Ile Trp Ala Gly Phe Cys Thr Trp Ile Ser Ser Leu
            100                 105                 110

Val Arg Ile Glu Asn Ser Tyr Ala Trp Gly Leu Ala Gly Tyr Thr Ala
        115                 120                 125

Leu Ile Ile Val Ile Thr Ile Gln Pro Glu Pro Leu Leu Thr Pro Gln
    130                 135                 140

Phe Ala Val Glu Arg Cys Ser Glu Ile Val Ile Gly Ile Val Cys Ala
145                 150                 155                 160

Ile Met Ala Asp Leu Leu Phe Ser Pro Arg Ser Ile Lys Gln Glu Val
                165                 170                 175

Asp Arg Glu Leu Glu Ser Leu Leu Val Ala Gln Tyr Gln Leu Met Gln
            180                 185                 190

Leu Cys Ile Lys His Gly Asp Gly Glu Val Val Asp Lys Ala Trp Gly
        195                 200                 205
```

-continued

Asp Leu Val Arg Arg Thr Thr Ala Leu Gln Gly Met Arg Ser Asn Leu
    210                 215                 220

Asn Met Glu Ser Ser Arg Trp Ala Arg Ala Asn Arg Arg Leu Lys Ala
225                 230                 235                 240

Ile Asn Thr Leu Ser Leu Thr Leu Ile Thr Gln Ser Cys Glu Thr Tyr
                245                 250                 255

Leu Ile Gln Asn Thr Arg Pro Glu Leu Ile Thr Asp Thr Phe Arg Glu
            260                 265                 270

Phe Phe Asp Thr Pro Val Glu Thr Ala Gln Asp Val His Lys Gln Leu
        275                 280                 285

Lys Arg Leu Arg Arg Val Ile Ala Trp Thr Gly Glu Arg Glu Thr Pro
290                 295                 300

Val Thr Ile Tyr Ser Trp Val Ala Ala Ala Thr Arg Tyr Gln Leu Leu
305                 310                 315                 320

Lys Arg Gly Val Ile Ser Asn Thr Lys Ile Asn Ala Thr Glu Glu Glu
                325                 330                 335

Ile Leu Gln Gly Glu Pro Glu Val Lys Val Glu Ser Ala Glu Arg His
            340                 345                 350

His Ala Met Val Asn Phe Trp Arg Thr Thr Leu Ser Cys Ile Leu Gly
        355                 360                 365

Thr Leu Phe Trp Leu Trp Thr Gly Trp Thr Ser Gly Ser Gly Ala Met
370                 375                 380

Val Met Ile Ala Val Val Thr Ser Leu Ala Met Arg Leu Pro Asn Pro
385                 390                 395                 400

Arg Met Val Ala Ile Asp Phe Ile Tyr Gly Thr Leu Ala Ala Leu Pro
                405                 410                 415

Leu Gly Leu Leu Tyr Phe Leu Val Ile Pro Asn Thr Gln Gln Ser
            420                 425                 430

Met Leu Leu Leu Cys Ile Ser Leu Ala Val Leu Gly Phe Phe Leu Gly
        435                 440                 445

Ile Glu Val Gln Lys Arg Arg Leu Gly Ser Met Gly Ala Leu Ala Ser
450                 455                 460

Thr Ile Asn Ile Ile Val Leu Asp Asn Pro Met Thr Phe His Phe Ser
465                 470                 475                 480

Gln Phe Leu Asp Ser Ala Leu Gly Gln Ile Val Gly Cys Val Leu Ala
                485                 490                 495

Phe Thr Val Ile Leu Leu Val Arg Asp Lys Ser Arg Asp Arg Thr Gly
            500                 505                 510

Arg Val Leu Leu Asn Gln Phe Val Ser Ala Val Ser Ala Met Thr
        515                 520                 525

Thr Asn Val Ala Arg Arg Lys Glu Asn His Leu Pro Ala Leu Tyr Gln
530                 535                 540

Gln Leu Phe Leu Leu Met Asn Lys Phe Pro Gly Asp Leu Pro Lys Phe
545                 550                 555                 560

Arg Leu Ala Leu Thr Met Ile Ile Ala His Gln Arg Leu Arg Asp Ala
                565                 570                 575

Pro Ile Pro Val Asn Glu Asp Leu Ser Ala Phe His Arg Gln Met Arg
            580                 585                 590

Arg Thr Ala Asp His Val Ile Ser Ala Arg Ser Asp Asp Lys Arg Arg
        595                 600                 605

Arg Tyr Phe Gly Gln Leu Leu Glu Glu Leu Glu Ile Tyr Gln Glu Lys
610                 615                 620

```
Leu Arg Ile Trp Gln Ala Pro Pro Gln Val Thr Glu Pro Val Asn Arg
625                 630                 635                 640

Leu Ala Gly Met Leu His Lys Tyr Gln His Ala Leu Thr Asp Ser
            645                 650                 655

<210> SEQ ID NO 9
<211> LENGTH: 347
<212> TYPE: PRT
<213> ORGANISM: Trichoderma reesei

<400> SEQUENCE: 9

Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345
```

<210> SEQ ID NO 10
<211> LENGTH: 766
<212> TYPE: PRT
<213> ORGANISM: Fusarium verticilloides

<400> SEQUENCE: 10

```
Met Leu Leu Asn Leu Gln Val Ala Ala Ser Ala Leu Ser Leu Ser Leu
1               5                   10                  15

Leu Gly Gly Leu Ala Glu Ala Ala Thr Pro Tyr Thr Leu Pro Asp Cys
            20                  25                  30

Thr Lys Gly Pro Leu Ser Lys Asn Gly Ile Cys Asp Thr Ser Leu Ser
        35                  40                  45

Pro Ala Lys Arg Ala Ala Ala Leu Val Ala Ala Leu Thr Pro Glu Glu
    50                  55                  60

Lys Val Gly Asn Leu Val Ser Asn Ala Thr Gly Ala Pro Arg Ile Gly
65                  70                  75                  80

Leu Pro Arg Tyr Asn Trp Trp Asn Glu Ala Leu His Gly Leu Ala Gly
                85                  90                  95

Ser Pro Gly Gly Arg Phe Ala Asp Thr Pro Pro Tyr Asp Ala Ala Thr
            100                 105                 110

Ser Phe Pro Met Pro Leu Leu Met Ala Ala Ala Phe Asp Asp Asp Leu
        115                 120                 125

Ile His Asp Ile Gly Asn Val Val Gly Thr Glu Ala Arg Ala Phe Thr
    130                 135                 140

Asn Gly Gly Trp Arg Gly Val Asp Phe Trp Thr Pro Asn Val Asn Pro
145                 150                 155                 160

Phe Lys Asp Pro Arg Trp Gly Arg Gly Ser Glu Thr Pro Gly Glu Asp
                165                 170                 175

Ala Leu His Val Ser Arg Tyr Ala Arg Tyr Ile Val Arg Gly Leu Glu
            180                 185                 190

Gly Asp Lys Glu Gln Arg Arg Ile Val Ala Thr Cys Lys His Tyr Ala
        195                 200                 205

Gly Asn Asp Phe Glu Asp Trp Gly Gly Phe Thr Arg His Asp Phe Asp
    210                 215                 220

Ala Lys Ile Thr Pro Gln Asp Leu Ala Glu Tyr Tyr Val Arg Pro Phe
225                 230                 235                 240

Gln Glu Cys Thr Arg Asp Ala Lys Val Gly Ser Ile Met Cys Ala Tyr
                245                 250                 255

Asn Ala Val Asn Gly Ile Pro Ala Cys Ala Asn Ser Tyr Leu Gln Glu
            260                 265                 270

Thr Ile Leu Arg Gly His Trp Asn Trp Thr Arg Asp Asn Asn Trp Ile
        275                 280                 285

Thr Ser Asp Cys Gly Ala Met Gln Asp Ile Trp Gln Asn His Lys Tyr
    290                 295                 300

Val Lys Thr Asn Ala Glu Gly Ala Gln Val Ala Phe Glu Asn Gly Met
305                 310                 315                 320

Asp Ser Ser Cys Glu Tyr Thr Thr Ser Asp Val Ser Asp Ser Tyr
                325                 330                 335

Lys Gln Gly Leu Leu Thr Glu Lys Leu Met Asp Arg Ser Leu Lys Arg
            340                 345                 350

Leu Phe Glu Gly Leu Val His Thr Gly Phe Phe Asp Gly Ala Lys Ala
        355                 360                 365

Gln Trp Asn Ser Leu Ser Phe Ala Asp Val Asn Thr Lys Glu Ala Gln
    370                 375                 380
```

```
Asp Leu Ala Leu Arg Ser Ala Val Glu Gly Ala Val Leu Leu Lys Asn
385                 390                 395                 400

Asp Gly Thr Leu Pro Leu Lys Leu Lys Lys Asp Ser Val Ala Met
            405                 410                 415

Ile Gly Phe Trp Ala Asn Asp Thr Ser Lys Leu Gln Gly Gly Tyr Ser
            420                 425                 430

Gly Arg Ala Pro Phe Leu His Ser Pro Leu Tyr Ala Ala Glu Lys Leu
            435                 440                 445

Gly Leu Asp Thr Asn Val Ala Trp Gly Pro Thr Leu Gln Asn Ser Ser
            450                 455                 460

Ser His Asp Asn Trp Thr Thr Asn Ala Val Ala Ala Lys Lys Ser
465                 470                 475                 480

Asp Tyr Ile Leu Tyr Phe Gly Leu Asp Ala Ser Ala Ala Gly Glu
            485                 490                 495

Asp Arg Asp Arg Glu Asn Leu Asp Trp Pro Glu Ser Gln Leu Thr Leu
            500                 505                 510

Leu Gln Lys Leu Ser Ser Leu Gly Lys Pro Leu Val Ile Gln Leu
            515                 520                 525

Gly Asp Gln Val Asp Asp Thr Ala Leu Leu Lys Asn Lys Lys Ile Asn
530                 535                 540

Ser Ile Leu Trp Val Asn Tyr Pro Gly Gln Asp Gly Gly Thr Ala Val
545                 550                 555                 560

Met Asp Leu Leu Thr Gly Arg Lys Ser Pro Ala Gly Arg Leu Pro Val
            565                 570                 575

Thr Gln Tyr Pro Ser Lys Tyr Thr Glu Gln Ile Gly Met Thr Asp Met
            580                 585                 590

Asp Leu Arg Pro Thr Lys Ser Leu Pro Gly Arg Thr Tyr Arg Trp Tyr
            595                 600                 605

Ser Thr Pro Val Leu Pro Tyr Gly Phe Gly Leu His Tyr Thr Lys Phe
            610                 615                 620

Gln Ala Lys Phe Lys Ser Asn Lys Leu Thr Phe Asp Ile Gln Lys Leu
625                 630                 635                 640

Leu Lys Gly Cys Ser Ala Gln Tyr Ser Asp Thr Cys Ala Leu Pro Pro
            645                 650                 655

Ile Gln Val Ser Val Lys Asn Thr Gly Arg Ile Thr Ser Asp Phe Val
            660                 665                 670

Ser Leu Val Phe Ile Lys Ser Glu Val Gly Pro Lys Pro Tyr Pro Leu
            675                 680                 685

Lys Thr Leu Ala Ala Tyr Gly Arg Leu His Asp Val Ala Pro Ser Ser
690                 695                 700

Thr Lys Asp Ile Ser Leu Glu Trp Thr Leu Asp Asn Ile Ala Arg Arg
705                 710                 715                 720

Gly Glu Asn Gly Asp Leu Val Val Tyr Pro Gly Thr Tyr Thr Leu Leu
            725                 730                 735

Leu Asp Glu Pro Thr Gln Ala Lys Ile Gln Val Thr Leu Thr Gly Lys
            740                 745                 750

Lys Ala Ile Leu Asp Lys Trp Pro Gln Asp Pro Lys Ser Ala
            755                 760                 765

<210> SEQ ID NO 11
<211> LENGTH: 350
<212> TYPE: PRT
<213> ORGANISM: Fusarium verticillioides
```

<400> SEQUENCE: 11

```
Met Gln Leu Lys Phe Leu Ser Ser Ala Leu Leu Ser Leu Thr Gly
1               5                   10                  15

Asn Cys Ala Ala Gln Asp Thr Asn Asp Ile Pro Pro Leu Ile Thr Asp
            20                  25                  30

Leu Trp Ser Ala Pro Ser Ala His Val Phe Glu Gly Lys Leu Trp
        35                  40                  45

Val Tyr Pro Ser His Asp Ile Glu Ala Asn Val Val Asn Gly Thr Gly
    50                  55                  60

Gly Ala Gln Tyr Ala Met Arg Asp Tyr His Thr Tyr Ser Met Lys Thr
65                  70                  75                  80

Ile Tyr Gly Lys Asp Pro Val Ile Asp His Gly Val Ala Leu Ser Val
                85                  90                  95

Asp Asp Val Pro Trp Ala Lys Gln Gln Met Trp Ala Pro Asp Ala Ala
            100                 105                 110

Tyr Lys Asn Gly Lys Tyr Tyr Leu Tyr Phe Pro Ala Lys Asp Lys Asp
        115                 120                 125

Glu Ile Phe Arg Ile Gly Val Ala Val Ser Asn Lys Pro Ser Gly Pro
    130                 135                 140

Phe Lys Ala Asp Lys Ser Trp Ile Pro Gly Thr Tyr Ser Ile Asp Pro
145                 150                 155                 160

Ala Ser Tyr Val Asp Thr Asn Gly Glu Ala Tyr Leu Ile Trp Gly Gly
                165                 170                 175

Ile Trp Gly Gly Gln Leu Gln Ala Trp Gln Asp His Lys Thr Phe Asn
            180                 185                 190

Glu Ser Trp Leu Gly Asp Lys Ala Ala Pro Asn Gly Thr Asn Ala Leu
        195                 200                 205

Ser Pro Gln Ile Ala Lys Leu Ser Lys Asp Met His Lys Ile Thr Glu
    210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Val His
                245                 250                 255

Lys Arg Gly Lys Leu Tyr Tyr Leu Met Tyr Ser Thr Gly Asp Thr His
            260                 265                 270

Phe Leu Val Tyr Ala Thr Ser Lys Asn Ile Tyr Gly Pro Tyr Thr Tyr
        275                 280                 285

Gln Gly Lys Ile Leu Asp Pro Val Asp Gly Trp Thr Thr His Gly Ser
    290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asp Gly Lys Ile Leu Leu Thr Arg Pro Lys Ile
            340                 345                 350
```

<210> SEQ ID NO 12
<211> LENGTH: 660
<212> TYPE: PRT
<213> ORGANISM: Fusarium verticillioides

<400> SEQUENCE: 12

```
Met Val Arg Phe Ser Ser Ile Leu Ala Ala Ala Cys Phe Val Ala
1               5                   10                  15

Val Glu Ser Val Asn Ile Lys Val Asp Ser Lys Gly Gly Asn Ala Thr
            20                  25                  30

Ser Gly His Gln Tyr Gly Phe Leu His Glu Asp Ile Asn Asn Ser Gly
            35                  40                  45

Asp Gly Gly Ile Tyr Ala Glu Leu Ile Arg Asn Arg Ala Phe Gln Tyr
            50                  55                  60

Ser Lys Lys Tyr Pro Val Ser Leu Ser Gly Trp Arg Pro Ile Asn Asp
65                  70                  75                  80

Ala Lys Leu Ser Leu Asn Arg Leu Asp Thr Pro Leu Ser Asp Ala Leu
                85                  90                  95

Pro Val Ser Met Asn Val Lys Pro Gly Lys Gly Lys Ala Lys Glu Ile
            100                 105                 110

Gly Phe Leu Asn Glu Gly Tyr Trp Gly Met Asp Val Lys Lys Gln Lys
            115                 120                 125

Tyr Thr Gly Ser Phe Trp Val Lys Gly Ala Tyr Lys Gly His Phe Thr
            130                 135                 140

Ala Ser Leu Arg Ser Asn Leu Thr Asp Asp Val Phe Gly Ser Val Lys
145                 150                 155                 160

Val Lys Ser Lys Ala Asn Lys Lys Gln Trp Val His Glu Phe Val
                165                 170                 175

Leu Thr Pro Asn Lys Asn Ala Pro Asn Ser Asn Asn Thr Phe Ala Ile
            180                 185                 190

Thr Tyr Asp Pro Lys Gly Ala Asp Gly Ala Leu Asp Phe Asn Leu Ile
            195                 200                 205

Ser Leu Phe Pro Pro Thr Tyr Lys Gly Arg Lys Asn Gly Leu Arg Val
210                 215                 220

Asp Leu Ala Glu Ala Leu Glu Gly Leu His Pro Ser Leu Leu Arg Phe
225                 230                 235                 240

Pro Gly Gly Asn Met Leu Glu Gly Asn Thr Asn Lys Thr Trp Trp Asp
            245                 250                 255

Trp Lys Asp Thr Leu Gly Pro Leu Arg Asn Arg Pro Gly Phe Glu Gly
            260                 265                 270

Val Trp Asn Tyr Gln Gln Thr His Gly Leu Gly Ile Leu Glu Tyr Leu
            275                 280                 285

Gln Trp Ala Glu Asp Met Asn Leu Glu Ile Ile Val Gly Val Tyr Ala
            290                 295                 300

Gly Leu Ser Leu Asp Gly Ser Val Thr Pro Lys Asp Gln Leu Gln Pro
305                 310                 315                 320

Leu Ile Asp Asp Ala Leu Asp Glu Ile Glu Phe Ile Arg Gly Pro Val
                325                 330                 335

Thr Ser Lys Trp Gly Lys Lys Arg Ala Glu Leu Gly His Pro Lys Pro
            340                 345                 350

Phe Arg Leu Ser Tyr Val Glu Val Gly Asn Glu Asp Trp Leu Ala Gly
            355                 360                 365

Tyr Pro Thr Gly Trp Asn Ser Tyr Lys Glu Tyr Arg Phe Pro Met Phe
            370                 375                 380

Leu Glu Ala Ile Lys Lys Ala His Pro Asp Leu Thr Val Ile Ser Ser
385                 390                 395                 400

Gly Ala Ser Ile Asp Pro Val Gly Lys Lys Asp Ala Gly Phe Asp Ile
                405                 410                 415
```

```
Pro Ala Pro Gly Ile Gly Asp Tyr His Pro Tyr Arg Glu Pro Asp Val
            420                 425                 430

Leu Val Glu Glu Phe Asn Leu Phe Asp Asn Asn Lys Tyr Gly His Ile
        435                 440                 445

Ile Gly Glu Val Ala Ser Thr His Pro Asn Gly Gly Thr Gly Trp Ser
    450                 455                 460

Gly Asn Leu Met Pro Tyr Pro Trp Trp Ile Ser Gly Val Gly Glu Ala
465                 470                 475                 480

Val Ala Leu Cys Gly Tyr Glu Arg Asn Ala Asp Arg Ile Pro Gly Thr
            485                 490                 495

Phe Tyr Ala Pro Ile Leu Lys Asn Glu Asn Arg Trp Gln Trp Ala Ile
            500                 505                 510

Thr Met Ile Gln Phe Ala Ala Asp Ser Ala Met Thr Thr Arg Ser Thr
        515                 520                 525

Ser Trp Tyr Val Trp Ser Leu Phe Ala Gly His Pro Met Thr His Thr
        530                 535                 540

Leu Pro Thr Thr Ala Asp Phe Asp Pro Leu Tyr Tyr Val Ala Gly Lys
545                 550                 555                 560

Asn Glu Asp Lys Gly Thr Leu Ile Trp Lys Gly Ala Ala Tyr Asn Thr
            565                 570                 575

Thr Lys Gly Ala Asp Val Pro Val Ser Leu Ser Phe Lys Gly Val Lys
            580                 585                 590

Pro Gly Ala Gln Ala Glu Leu Thr Leu Leu Thr Asn Lys Glu Lys Asp
        595                 600                 605

Pro Phe Ala Phe Asn Asp Pro His Lys Gly Asn Asn Val Val Asp Thr
    610                 615                 620

Lys Lys Thr Val Leu Lys Ala Asp Gly Lys Gly Ala Phe Asn Phe Lys
625                 630                 635                 640

Leu Pro Asn Leu Ser Val Ala Val Leu Glu Thr Leu Lys Lys Gly Lys
            645                 650                 655

Pro Tyr Ser Ser
            660
```

US 8,476,048 B2

XYLOSE UTILIZING ZYMOMONAS MOBILIS WITH IMPROVED ETHANOL PRODUCTION IN BIOMASS HYDROLYSATE MEDIUM

STATEMENT OF GOVERNMENT RIGHTS

This invention was made with United States Government support under Award No. DE-FC36-07GO17056 awarded by the Department of Energy. The U.S. Government has certain rights in this invention.

FIELD OF THE INVENTION

The invention relates to the fields of microbiology and fermentation. More specifically, mutant *Zymomonas* strains with improved growth and ethanol production in biomass hydrolysate medium were isolated and characterized.

BACKGROUND OF THE INVENTION

Production of ethanol by microorganisms provides an alternative energy source to fossil fuels and is therefore an important area of current research. It is desirable that microorganisms producing ethanol, as well as other useful products, be capable of growing and producing ethanol in a medium that does not impact the human food supply, such as avoiding use of sugars produced from corn grain. As a result of developments in cellulosic biomass processing, glucose, xylose, and other sugars may be released in high concentrations in a biomass hydrolysate for use in fermentation. As such, conversion of biomass to ethanol poses great possibility for improving environmental impacts by using renewable non-food resources to provide an alternative to fossil fuels.

*Zymomonas mobilis* and other bacterial ethanologens which do not naturally utilize xylose have been genetically engineered for xylose utilization to improve growth and ethanol production by using more of the sugars in biomass hydrolysate. However, growth and ethanol production in biomass-hydrolysate containing medium is typically not optimal due to the presence of acetate and other compounds that are inhibitory to microorganisms. Disclosed in commonly owned and co-pending United States Patent Publication US20110014670A1 is a method for producing an improved xylose-utilizing *Zymomonas* strain that is more tolerant to acetate and ethanol in the medium, as well as strains isolated by the method.

The toxic effect of single compounds likely to be found in the hydrolysates of pretreated biomass is described in Delegenes et al. ((1996) Enzymes and Microbial Technology 19:220-224). Adaptation of xylose-fermenting *Zymomonas mobilis* to conditioned dilute acid yellow poplar hemicellulose hydrolysate is described in Lawford et al. ((1999), Applied Biochemistry and Biotechnology 77:191-204).

There remains a need for isolated xylose-utilizing *Zymomonas* ethanologen strains with improved ethanol production during fermentation in biomass hydrolysate medium, and methods for genetic engineering to produce improved strains.

SUMMARY OF THE INVENTION

The invention provides recombinant xylose-utilizing *Zymomonas* strains with improved growth and ethanol production in biomass hydrolysate medium. In addition, the invention provides methods of making improved *Zymomonas* strains for use in hydrolysate medium and methods of making ethanol using said strains.

Accordingly, the invention provides a recombinant, xylose-utilizing, ethanol-producing microorganism of the genus *Zymomonas*, having at least one genetic modification in the zmo1432 open reading frame.

In one aspect the invention provides a polypeptide having an amino acid sequence selected from the group consisting of SEQ ID NO: 3 and SEQ ID NO: 4, and polynucleotides encoding the same.

In another aspect the invention provides a method for the production of a recombinant *Zymonomas* ethanologen comprising:
  a) providing a xylose-utilizing, ethanol-producing microorganism of the genus *Zymomonas*;
  b) providing a polynucleotide encoding a protein having the amino acid sequence selected from the group consisting of: SEQ ID NO:3 and SEQ ID NO:4; and
  c) introducing the polynucleotide of b) into the microorganism of a);
  wherein the endogenous zmo1432 coding region is disrupted.

In an alternate aspect the invention provides a method for the production of a recombinant *Zymonomas* ethanologen comprising:
  a) providing a xylose-utilizing, ethanol-producing microorganism of the genus *Zymomonas* comprising a zmo1432 open reading frame encoding a polypeptide having the amino acid sequence as set forth in SEQ ID NO: 2; and
  b) introducing a mutation in the zmo1432 open reading frame of a) such that expression of the mutated open reading frame expresses a polypeptide having an amino acid sequence selected from the group consisting of SEQ ID NO:3 and SEQ ID NO:4.

In another aspect the invention provides a method for the production of ethanol comprising:
  a) providing the recombinant *Zymomonas* of the invention;
  b) providing a biomass hydrolysate medium comprising xylose; and
  c) growing the *Zymomonas* of a) in the biomass hydrolysate medium of b) wherein ethanol is produced.

BRIEF DESCRIPTION OF THE FIGURES, BIOLOGICAL DEPOSITS AND SEQUENCE DESCRIPTIONS

Applicants have made the following biological deposits under the terms of the Budapest Treaty on the International Recognition of the Deposit of Microorganisms for the Purposes of Patent Procedure:

Information on Deposited Strains

| Depositor Identification Reference | International Depository Designation | Date of Deposit |
|---|---|---|
| *Zymomonas* ZW658 | ATCC No PTA-7858 | Sep. 12, 2006 |

FIG. 3 shows an alignment of the protein encoded by zmo1432 and the Bcemn03_1426 protein of *Burkholderia cenocepacia*.

FIG. 4 shows an alignment of the protein encoded by zmo1432 and the *E. coli* AaeB protein.

Figure 1:
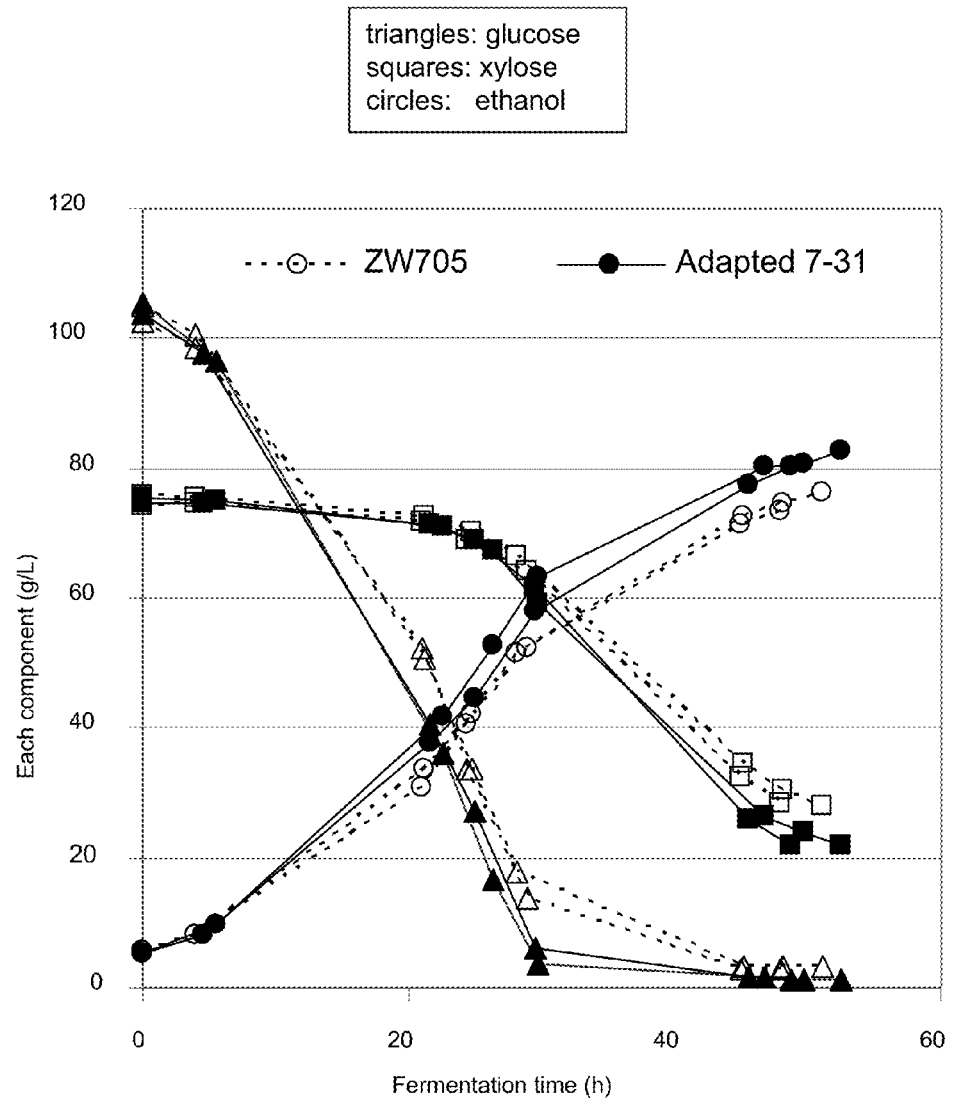
FIG. 1 shows a graph of fermentation of corn cob hydrolysate over time, comparing glucose and xylose utilization and ethanol production for *Zymomonas* strains and Adapted 7-31.

The following sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO:1 is the nucleotide sequence of the coding region designated zmo1432 in the published *Zymomonas mobilis* genomic sequence (NCBI Reference: NC_006526.2).

SEQ ID NO:2 is the amino acid sequence encoded by the coding region designated zmo1432 in the published *Zymomonas mobilis* genomic sequence (NCBI Reference: NC_006526.2).

SEQ ID NO:3 is the amino acid sequence of SEQ ID NO:2 but with the amino acid at position No. 366 changed to arginine.

SEQ ID NO:4 is the amino acid sequence of SEQ ID NO:2 but with the amino acid at position No. 117 changed to phenylalanine.

SEQ ID NO:5 is the amino acid sequence of the *Burkholderia cenocepacia* protein encoded by fusC (Accession P24128).

SEQ ID NO:6 is the amino acid sequence of the *Klebsiella oxytoca* fusaric acid detoxification protein (Accession: Q48403)

SEQ ID NO:7 is the amino acid sequence of the *Burkholderia cenocepacia* protein encoded by Bcenmc03_1426. SEQ ID NO:8 is the amino acid sequence of the *E. coli* protein AaeB.

SEQ ID NO:9 is the amino acid sequence of the immature Xyn3 which incorporates a predicted signal sequence corresponding to positions 1 to 16.

SEQ ID NO:10 is the amino acid sequence of the immature Fv3A which incorporates a predicted signal sequence corresponding to positions 1 to 23.

SEQ ID NO:11 is the amino acid sequence of the immature Fv43D, which incorporates a predicted signal sequence corresponding to positions 1 to 20.

SEQ ID NO:12 is the amino acid sequence of the immature Fv51A which incorporates a predicted signal sequence corresponding to positions 1 to 19.

DETAILED DESCRIPTION

The present invention describes adaptation of xylose-utilizing *Zymomonas* cells in biomass hydrolysate medium, to improve growth and ethanol production. Characterization of mutations in adapted strains identified mutations characteristic for the improvement, which may be engineered in non-adapted xylose-utilizing *Zymomonas* strains. These strains are used to make ethanol more efficiently, to produce ethanol as a fossil fuel replacement.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein "xylose-utilizing *Zymomonas* cell(s)" refers to a cell or cells of a strain that are genetically engineered to express enzymes conferring the ability to use xylose as a carbohydrate source for fermentation.

The term "adapted strain" refers to a microorganism that has been selected for growth under particular conditions in order to improve it's ability to grow and produce a product in those conditions.

As used herein "corresponding non-adapted strain" refers to the original xylose-utilizing *Zymomonas* strain that is a strain from which improved strains are produced using the biomass hydrolysate adaptation process disclosed herein.

As used herein "feeding growth medium" refers to the medium that is added into the continuous culture vessel.

The term "lignocellulosic biomass" or "biomass" refers to any lignocellulosic material and includes materials comprising cellulose, hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Lignocellulosic biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses, wheat straw, barley straw, hay, rice straw, switchgrass, waste paper, sugar cane bagasse, sorghum plant material, soybean plant material, components obtained from milling of grains, trees, branches, roots, leaves, wood chips, sawdust, shrubs and bushes, vegetables, fruits, and flowers.

As used herein "biomass hydrolysate" and "cellulosic hydrolysate" refer to a product produced from biomass, which is cellulosic material, typically through pretreatment and saccharification processes. Fermentable sugars are present in the hydrolysate, as well as other products.

As used herein "biomass hydrolysate medium" refers to medium which contains at least about 50% hydrolysate prepared from cellulosic and/or lignocellulosic biomass. Hydrolysate is prepared by saccharification of biomass, typically preceded by pretreatment. In addition to the hydrolysate, the medium may include defined components for biocatalyst growth and production.

"Xyn3" is a GH10 family xylanase from *Trichoderma reesei*. Xyn3 (SEQ ID NO:9) was shown to have endoxylanase activity indirectly by observation of its ability to catalyze increased xylose monomer production in the presence of xylobiosidase when the enzymes act on pretreated biomass or on isolated hemicellulose.

"Fv3A" is a GH3 family enzyme from *Fusarium verticillioides*. Fv3A (SEQ ID NO:10) was shown to have β-xylosidase activity, for example, in an enzymatic assay using p-nitrophenyl-β-xylopyranoside, xylobiose, mixed linear xylo-oligomers, branched arabinoxylan oligomers from hemicellulose, or dilute ammonia pretreated corncob as substrates.

"Fv43D" is a GH43 family enzyme from *Fusarium verticillioides*. Fv43D (SEQ ID NO:11) was shown to have β-xylosidase activity in, for example, an enzymatic assay using p-nitrophenyl-β-xylopyranoside, xylobiose, and/or mixed, linear xylo-oligomers as substrates.

"Fv51A" is a GH51 family enzyme from *Fusarium verticillioides*. Fv51A (SEQ ID NO:12) was shown to have L-α-arabinofuranosidase activity in, for example, an enzymatic assay using 4-nitrophenyl-α-L-arabinofuranoside as a substrate.

"Gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "genetic construct" refers to a nucleic acid fragment that encodes for expression of one or more specific proteins or functional RNA molecules. In the gene construct the gene may be native, chimeric, or foreign in nature. Typically a genetic construct will comprise a "coding sequence". A "coding sequence" refers to a DNA sequence that encodes a specific amino acid sequence.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Protects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS*. 5:151-153 (1989); Higgins, D. G. et al., *Comput. Appl. Biosci.*, 8:189-

191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS*. 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Producing *Zymomonas* Strains with Improved Fermentation in Hydrolysate Medium

The invention provides a recombinant, xylose-utilizing, ethanol-producing microorganism of the genus *Zymomonas*, having at least one genetic modification in the zmo1432 open reading frame. The effect of this mutation is to express a polypeptide that improves the behavior of the strain in a hydrolysate medium, increasing the strain's tolerance to various growth inhibitors in the hydrolysate and increasing the yield of ethanol. The improvements in fermentation behavior have been linked to mutations in the zmo 1432 region of the *Zymomonas* genome, (NCBI Reference: NC_006526.2), defined herein as SEQ ID NO:1, encoding the polypeptide of SEQ ID NO:2.

Accordingly it is put forth here that improved fermentation in hydrolysate medium may be conferred to *Zymomonas* strains that are able to utilize xylose as a carbon source and that produce ethanol by introducing at least one genetic modification in an open reading frame (ORF) that encodes a protein having at least about 95% amino acid identity to SEQ ID NO:2, prior to modification. The protein may have at least about 95%, 96%, 96%, 98%, 99%, or 100% identity to SEQ ID NO:2. Any genetic modification in said protein may be made which increases ethanol production by the strain harboring said mutant protein in the presence of hydrolysate medium. Increase in ethanol production is determined by comparison to production by a *Zymomonas* strain lacking the genetic modification, under the same conditions of fermentation. A strain with a genetic modification in said ORF may be readily assayed by one of skill in the art to assess increased ethanol production in the presence of biomass hydrolysate by methods such as described in Example 3 herein. Said improved strain has higher tolerance to biomass hydrolysate, and inhibitors present in biomass hydrolysate, where tolerance refers to the ability of the strain to grow and produce ethanol similarly in media with a specified level of hydrolysate (level of tolerance) as compared to in media with less or no hydrolysate. Higher tolerance is determined by comparison with a *Zymomonas* strain lacking the genetic modification.

In one embodiment the genetic modification results in an alteration at position 366 of the amino acid sequence of SEQ ID NO:2 that substitutes arginine for threonine. In another embodiment the genetic modification results in an alteration at position 117 of the amino acid sequence of SEQ ID NO:2 that substitutes phenylalanine for serine. Any change may be made in the nucleotide sequence which results in the change of codon 366 to encode arginine, or results in the change of codon 117 to encode phenylalanine. Codons encoding arginine are CGT, CGC, CGA, CGG, AGA, and AGG. Codons encoding phenylalanine are TTT and TTC.

In one embodiment the genetic modification is in a coding region that has at least 95% sequence identity to the ORF zmo1432 as named in the published *Zymomonas mobilis* genomic sequence (NCBI Reference: NC_006526.2) which is the complement of nucleotides 1446603 to 1448633 having SEQ ID NO:1. The ORF of SEQ ID NO:1 may be called alternative names, but in any case it may be identified as zmo1432 by comparison to the sequence of SEQ ID NO:1. There may be some variation in the sequence of coding regions identified as zmo1432 among *Zymomonas* species or strains. Thus a coding region identified as zmo1432 may have at least about 95%, 96%, 97%, 98%, 99%, or 100% sequence identity to SEQ ID NO:1 and the coding region with the genetic modification may have at least about 95%, 96%, 97%, 98%, 99%, or 100% sequence identity to SEQ ID NO:1 prior to genetic modification. This coding region, prior to modification, is the target for genetic modification.

At least one of the described genetic modifications may be created in a *Zymomonas* strain that is able to utilize xylose as a carbon source and that produces ethanol by any method known to one of skill in the art. Such methods include by adaptation as described below and in Examples 1 and 2 herein, by chemical mutagenesis and screening, and by genetic engineering.

Genetic engineering to introduce a genetic modification in the target coding region may be by methods including using double-crossover homologous recombination to replace the endogenous target coding region with the same coding region harboring a mutation that is described above. In homologous recombination, DNA sequences flanking the target integration site are placed bounding a spectinomycin-resistance gene or other selectable marker, and the replacement mutant sequence leading to insertion of the selectable marker and the replacement mutant sequence into the target genomic site. The selectable marker is outside of the coding region so that in the product, the coding region is expressed. In addition, the selectable marker may be bounded by site-specific recombination sites, so that after expression of the corresponding site-specific recombinase, the resistance gene is excised from the genome. Particularly suitable for integration of a replacement mutant sequence is transposition using EPICENTRE®'s EZ::Tn in vitro transposition system, which is used in Examples 1 and 6 of United States Patent Publication US-2009-0246846-A1.

Alternatively, expression of the target endogenous coding region may be disrupted in a cell by a manipulation such as insertion, mutation, or deletion and a gene expressing the coding region harboring a mutation, as described above, may be introduced into the cell. An example of double-crossover, homologous recombination in *Zymomonas* used to inactivate a coding region is described in U.S. Pat. No. 7,741,119. The introduced gene may be the endogenous gene (with mutant coding region) including its native promoter, or the introduced gene may be a chimeric gene comprising an operably linked promoter and a coding region with at least about 95%, 96%, 97%, 98%, or 99% identity to the disrupted coding region. Typically a 3' termination region is included in a chimeric gene. Promoters that may be used in *Zymomonas* include ZmPgap and the promoter of the *Zymomonas* enolase gene.

The introduced gene may be maintained on a plasmid, or integrated into the genome using, for example, homologous recombination, site-directed integration, or random integration. A gene to be introduced is typically constructed in or transferred to a vector for further manipulations. Vectors are well known in the art. Particularly useful for expression in *Zymomonas* are vectors that can replicate in both *E. coli* and *Zymomonas*, such as pZB188 which is described in U.S. Pat. No. 5,514,583. Vectors may include plasmids for autonomous replication in a cell, and plasmids for carrying constructs to be integrated into bacterial genomes. Plasmids for DNA integration may include transposons, regions of nucleic acid sequence homologous to the target bacterial genome, or other sequences supporting integration. An additional type of vector may be a transposome produced using, for example, a system that is commercially available from EPICENTRE®. It is well known how to choose an appropriate vector for the desired target host and the desired function.

Host Strain

Any strain of *Zymomonas* that is able to utilize xylose as a carbon source and that produces ethanol may be a starting strain for the present invention. Such strains are used for adaptation in hydrolysate medium, for chemical mutagenesis and screening, or are genetically engineered to produce the improved strains disclosed herein. Strains of *Zymomonas*, such as *Z. mobilis*, that have been engineered to express a xylose to ethanol fermentation pathway are particularly useful. Endogenous genes may provide part of the metabolic pathway, or may be altered by any known genetic manipulation technique to provide a protein with enzyme activity useful for xylose metabolism. For example, the endogenous transketolase may complement other introduced enzyme activities in creating a xylose utilization pathway. Typically four genes may be introduced into a *Zymomonas* strain, such as *Z. mobilis*, for expression of four enzymes involved in xylose metabolism as described in U.S. Pat. No. 5,514,583, which is herein incorporated by reference. These include genes encoding xylose isomerase, which catalyzes the conversion of xylose to xylulose and xylulokinase, which phosphorylates xylulose to form xylulose 5-phosphate. In addition, transketolase and transaldolase, two enzymes of the pentose phosphate pathway, convert xylulose 5-phosphate to intermediates that couple pentose metabolism to the glycolytic Entner-Douderoff pathway permitting the metabolism of xylose to ethanol. DNA sequences encoding these enzymes may be obtained from any of numerous microorganisms that are able to metabolize xylose, such as enteric bacteria, and some yeasts and fungi. Sources for the coding regions include *Xanthomonas, Klebsiella, Escherichia, Rhodobacter, Flavobacterium, Acetobacter, Gluconobacter, Rhizobium, Agrobacterium, Salmonella, Pseudomonads*, and *Zymomonas*. Particularly useful are the coding regions of *E. coli*.

The encoding DNA sequences are operably linked to promoters that are expressed in *Z. mobilis* cells such as the promoters of *Z. mobilis* glyceraldehyde-3-phosphate dehydrogenase (GAP promoter), and *Z. mobilis* enolase (ENO promoter). The coding regions may individually be expressed from promoters, or two or more coding regions may be joined in an operon with expression from the same promoter. The resulting chimeric genes may be introduced into *Zymomonas* and maintained on a plasmid, or integrated into the genome using, for example, homologous recombination, site-directed integration, or random integration. Xylose-utilizing strains that are of particular use include ZM4(pZB5) (described in U.S. Pat. No. 5,514,583, U.S. Pat. No. 6,566,107, and U.S. Pat. No. 5,571,2133, and incorporated by reference herein), 8b (United States Patent Application U.S. 2003/0162271; Mohagheghi et al., (2004) Biotechnol. Lett. 25; 321-325), as well as ZW658 (ATCC PTA-7858), ZW800, ZW801-4, ZW801-5, and ZW801-6 (described in commonly owned and co-pending United States Patent Application Publication U.S. 2008-0286870 A1, which is herein incorporated by reference).

*Zymomonas* strains that are additionally engineered to utilize other sugars that are not natural substrates, may also be used in the present process. An example is a strain of *Z. mobilis* engineered for arabinose utilization as described in U.S. Pat. No. 5,843,760, which is herein incorporated by reference.

Adaptation

For adaptation, a xylose-utilizing strain of *Zymomonas* (a starting strain as described above) is continuously grown in a medium containing biomass hydrolysate. Biomass hydrolysate is produced by saccharification of biomass. Typically the biomass is pretreated prior to saccharification. Biomass may be treated by any method known by one skilled in the art to produce fermentable sugars in a hydrolysate. Typically the biomass is pretreated using physical and/or chemical treatments, and saccharified enzymatically. Physical and chemical treatments may include grinding, milling, cutting, base treatment such as with ammonia or NaOH, and acid treatment. Particularly useful is a low ammonia pretreatment where biomass is contacted with an aqueous solution comprising ammonia to form a biomass-aqueous ammonia mixture where the ammonia concentration is sufficient to maintain an alkaline pH of the biomass-aqueous ammonia mixture but is less than about 12 wt. % relative to dry weight of biomass, and where dry weight of biomass is at least about 15 wt % solids relative to the weight of the biomass-aqueous ammonia mixture, as disclosed in co-pending and commonly owned United States Patent Application Publication US-20070031918-A1, which is herein incorporated by reference.

Enzymatic saccharification typically makes use of an enzyme composition or blend to break down cellulose and/or hemicellulose and to produce a hydrolysate containing sugars such as, for example, glucose, xylose, and arabinose. Saccharification enzymes are reviewed in Lynd, L. R., et al. (Microbiol. Mol. Biol. Rev., 66:506-577, 2002). At least one enzyme is used, and typically a saccharification enzyme blend is used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3). Glycosidases useful in the present method can be categorized by the biomass components they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases).

In addition, it may be useful to add other activities to the saccharification enzyme consortium such as peptidases (EC 3.4.x.y), lipases (EC 3.1.1.x and 3.1.4.x), ligninases (EC 1.11.1.x), or feruloyl esterases (EC 3.1.1.73) to promote the release of polysaccharides from other components of the biomass. It is known in the art that microorganisms that produce polysaccharide-hydrolyzing enzymes often exhibit an activity, such as a capacity to degrade cellulose, which is catalyzed by several enzymes or a group of enzymes having different substrate specificities. Thus, a "cellulase" from a microorganism may comprise a group of enzymes, one or more or all of which may contribute to the cellulose-degrading activity. Commercial or non-commercial enzyme preparations, such as cellulase, may comprise numerous enzymes depending on the purification scheme utilized to obtain the enzyme.

Saccharification enzymes may be obtained commercially. Such enzymes include, for example, Spezyme® CP cellulase, Multifect® xylanase, Accelerase® 1500, and Accellerase® DUET (Danisco U.S. Inc., Genencor International, Rochester, N.Y.). In addition, saccharification enzymes may be unpurified and provided as a cell extract or a whole cell preparation. The enzymes may be produced using recombinant microorganisms that have been engineered to express one or more saccharifying enzymes.

Additional enzymes for saccharification include, for example, glycosyl hydrolases such as members of families GH3, GH39, GH43, GH55, GH10, and GH11. GHs are a group of enzymes that hydrolyze the glycosidic bond between two or more carbohydrates, or between a carbohydrate and a noncarbohydrate moiety. Families of GHs have been classified based on sequence similarity and the classification is available in the Carbohydrate-Active enzyme (CAZy) database (Cantarel et al. (2009) Nucleic Acids Res. 37 (Database issue):D233-238). Certain of these enzymes are able to act on various substrates and have demonstrated effecacy as saccharification enzymes. Glycoside hydrolase family 3 ("GH3") enzymes have a number of known activities, including, for example, β-glucosidase (EC:3.2.1.21); β-xylosidase (EC:3.2.1.37); N-acetyl β-glucosaminidase (EC: 3.2.1.52); glucan β-1,3-glucosidase (EC:3.2.1.58); cellodextrinase (EC:3.2.1.74); exo-1,3-1,4-glucanase (EC:3.2.1); and/or β-galactosidase (EC 3.2.1.23) activities. Glycoside hydrolase family 39 ("GH39") enzymes also have a number of known activities, including, for example, α-L-iduronidase (EC:3.2.1.76) and/or β-xylosidase (EC:3.2.1.37) activities. Glycoside hydrolase family 43 ("GH43") enzymes have a number of known activities including, for example, L-α-arabinofuranosidase (EC 3.2.1.55); β-xylosidase (EC 3.2.1.37); endoarabinanase (EC 3.2.1.99); and/or galactan 1,3-β-galactosidase (EC 3.2.1.145) activities. Glycoside hydrolase family 51 ("GH51") enzymes are known to have, for example, L-α-arabinofuranosidase (EC 3.2.1.55) and/or endoglucanase (EC 3.2.1.4) activities. Glycoside hydrolase family 10 ("GH10") have been described in detail in Schmidt et al., 1999, Biochemistry 38:2403-2412 and Lo Leggio et al., 2001, FEBS Lett 509: 303-308) and the Glycoside hydrolase family 11 ("GH11") have been described in Hakouvainen et al., 1996, Biochemistry 35:9617-24.

In the present adaptation process, xylose-utilizing Zymomonas is continuously grown in the presence of increasing proportions of biomass hydrolysate in the growth medium as described in Examples 1 and 2 herein. At periodic intervals samples are taken and assayed for performance in hydrolysate medium, including for xylose and glucose utilization, and for ethanol production. Multiple rounds of adaptation in a medium containing increasing proportions of hydrolysates, as well as other stress components such as acetate and ethanol, may be used to produce strains with improved performance, such as those described above.

Fermentation of Improved Xylose-Utilizing Strain

An engineered xylose-utilizing and ethanol producing Zymomonas strain with at least one genetic modification described herein may be used in fermentation to produce ethanol. The Z. mobilis strain is brought in contact with medium that contains biomass hydrolysate that includes sugars comprising glucose and xylose. At least a portion of the sugars are derived from pretreated and saccharified cellulosic or lignocellulosic biomass. Additional sugars and/or other media components may be included in the medium.

When the sugars concentration is high such that growth is inhibited, the medium includes sorbitol, mannitol, or a mixture thereof as disclosed in commonly owned U.S. Pat. No. 7,629,156. Galactitol or ribitol may replace or be combined with sorbitol or mannitol. The Z. mobilis grows in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. The fermentations may be run at temperatures that are between about 30° C. and about 37° C., at a pH of about 4.5 to about 7.5.

The present Z. mobilis may be grown in medium containing mixed sugars including xylose in laboratory scale fermenters, and in scaled up fermentation where commercial quantities of ethanol are produced. Where commercial production of ethanol is desired, a variety of culture methodologies may be applied. For example, large-scale production from the present Z. mobilis strains may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of ethanol.

A variation on the standard batch system is the Fed-Batch system. Fed-Batch culture processes are also suitable for growth of the present Z. mobilis strains and comprise a typical batch system with the exception that the substrate is added in increments as the culture progresses. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., Appl. Biochem. Biotechnol., 36, 227, (1992), herein incorporated by reference.

Commercial production of ethanol may also be accomplished with a continuous culture. Continuous cultures are open systems where culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Particularly suitable for ethanol production is a fermentation regime as follows. The desired Z. mobilis strain of the present invention is grown in shake flasks in semi-complex medium at about 30° C. to about 37° C. with shaking at about 150 rpm in orbital shakers and then transferred to a 10 L seed fermentor containing similar medium. The seed culture is grown in the seed fermentor anaerobically until $OD_{600}$ is between 3 and 10, when it is transferred to the production fermentor where the fermentation parameters are optimized for ethanol production. Typical inoculum volumes transferred from the seed tank to the production tank range from about 2% to about 20% v/v. Fermentation medium for the present strains contains biomass hydrolysate in at least about 50% and may be supplemented with other nutrients, as known to one of skill in the art. A final concentration of about 5 mM sorbitol or mannitol is present in the medium.

The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-35° C. In order to minimize foaming, antifoam agents (any class—silicone based, organic based etc) are added to the vessel as needed. An antibiotic, for which there is an antibiotic resistant marker in the strain or to which the strain is resistant, such as kanamycin, may be used optionally to minimize contamination.

Any set of conditions described above, and additionally variations in these conditions that are well known in the art, are suitable conditions for production of ethanol by a xylose-utilizing recombinant Zymomonas strain.

DESCRIPTION OF THE PREFERRED EMBODIMENTS

It is disclosed herein that xylose-utilizing Zymomonas strains with improved utilization of glucose and xylose, and production of ethanol, in the presence of biomass hydrolysate can be obtained by a process of adaptation and screening in biomass hydrolysate medium. Increase in glucose and xylose utilization, and ethanol production, is measured by comparison to glucose and xylose utilization by the xylose-utilizing corresponding non-adapted strain. The corresponding non-adapted strain is the strain used as the starting strain for the hydrolysate adaptation process.

Zymomonas mobilis strains were isolated from hydrolysate adaptation experiments as described in Examples 1 and 2 herein. Two isolated strains were named Adapted 5-6 (or AR25-6) and Adapted 7-31 (or AR37-31), and were further characterized. When grown in corn cob hydrolysate as described in Example 3 herein, these strains utilized glucose and xylose more rapidly than the corresponding non-adapted strain ZW705. At 21 hours of a fermentation run, about 20% more glucose had been utilized. In addition, at 21 hours about 22% more ethanol was produced, while at 52 hours about 21% more xylose had been used and 5% more ethanol was produced. In general, the exact percent increases in glucose utilization, xylose utilization, and ethanol production in a strain with new genetic changes of the Adapted 5-6 or Adapted 7-31 strains, that are described below, will depend on many factors. These factors include the conditions of the fermentation as well as the genetic characteristics of the strain that are in addition to the new genetic changes disclosed herein.

To identify any changes in the genomes of the Adapted 5-6 and Adapted 7-31 strains, the genomes were sequenced. By comparison of these genomic sequences to genomic sequences of the corresponding starting strain, ZW705 (described in United States Patent Publication US20110014670A1), wild type strain ZW1 (ATCC 31821), and the published Zymomonas mobilis sequence of strain ATCC 31821 (Seo et. al, Nat. Biotech. 23:63-8 2005; NCBI Reference: NC_006526.2), it was determined that both strains had a single, new mutation in the same coding region. This coding region is identified as the zmo1432 open reading frame (ORF) in the published Zymomonas mobilis genomic sequence (NCBI Reference: NC_006526.2) and is the complement of nucleotides 1446603 to 1448633 having SEQ ID NO:1.

Adapted 5-6 has a mutation at position No. 1097 in SEQ ID NO:1 that is a change from C to G. This results in the change of codon 366 from ACA encoding threonine to AGA encoding arginine in the zmo1432 encoded protein (SEQ ID NO:2) resulting in the protein of SEQ ID NO:3 where arginine is substituted for threonine No. 366. Adapted 7-31 has a mutation at position No. 350 in SEQ ID NO:1 that is a change from C to T. This results in the change of codon 117 from TCT encoding serine to TTT encoding phenylalanine in the zmo1432 encoded protein (SEQ ID NO:2)) resulting in the protein of SEQ ID NO:4 where phenylalanine is substituted for serine No. 117.

The hypothetical coding region zmo1432 (or ORF) is annotated in the Zymomonas mobilis complete genome sequence (NCBI Reference: NC_006526.2) as encoding a "fusaric acid resistance protein". It is annotated as having a fusaric acid resistance protein conserved region which is protein motif: PFAM:PF04632 (Wellcome Trust Sanger Institute, Genome Research Limited, Hinxton, England). This motif is found in proteins associated with fusaric acid resistance from Burkholderia cepacia (Swiss-Prot::P24128 (SEQ ID NO:5); Utsumi et al. (1991) Agric. Biol. Chem. 55:1913-1918; the organism was renamed from Pseudomonas cepacia) and Klebsiella oxytoca (Swiss-Prot::Q48403 (SEQ ID NO:6); Toyoda et al. (1991) J Phytopathol. 133:165-277), which are likely to be membrane transporter proteins.

A region named Bcenm03_1426 of the Burkholderia cepacia chromosome 1 complete sequence is annotated as encoding a putative fusaric acid resistance transporter protein (Accession YP_001764723; Copeland et al. submitted Feb. 27, 2008). This protein (SEQ ID NO:7) has similarity to the zmo1432 encoded protein as described in Example 4 herein. In addition, the E. coli protein AaeB (SEQ ID NO:8), which is a component of an aromatic carboxylic acid efflux pump (VanDyk et al J. Bact. 186:7196-7204 (2004)), has similarity to the zmo1432 encoded protein, as described in Example 4 herein. Thus a transporter protein of Zymomonas may be the target of mutations that improve glucose and xylose utilization, and ethanol production in xylose-utilizing Zymomonas strains that are grown in hydrolysate medium.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" means milliliter(s), "µL" or "µl" means microliter(s), "µg" means microgram(s), "ng" means nanogram(s), "g" means gram(s), "mM" means millimolar, "µM" means micromolar, "nm" means nanometer(s), "mmol" means micromole(s), "pmol" means picomole(s), "OD600" is optical density at 600 nm.

General Methods

Turbidostat

Adaptation was in a turbidostate (U.S. Pat. No. 6,686,194; Heurisko USA, Inc. Newark, Del.), which is a continuous flow culture device where the concentration of cells in the culture was kept constant by controlling the flow of medium into the culture, such that the turbidity of the culture was kept within specified narrow limits. Two media were available to the growing culture in the continuous culture device, a resting medium (Medium A) and a challenge medium (Medium B). A culture was grown on a resting medium in a growth chamber to a turbidity set point and then was diluted at a dilution rate set to maintain that cell density. Dilution was performed by adding media at a defined volume once every 10 minutes. When the turbidostat entered a media challenge mode, the choice of adding challenge medium or a resting medium was made based on the rate of return to the set point after the previous media addition. The steady state concentration of medium in the growth chamber was a mix of Medium A and Medium B, with the proportions of the two media dependent upon the rate of draw from each medium that allowed maintenance of the set cell density at the set dilution rate. A sample of cells representative of the population in the growth chamber was recovered from the outflow of the turbidostat (in a trap chamber) at weekly intervals. The cell sample was grown once in MRM3G6 medium and saved as a glycerol stock at −80° C.

Enzymes

Spezyme® CP-100, Multifect® CX12L, and Accellerase® 1500 were from Danisco U.S. Inc., Genencor (Rochester, N.Y.).

Novozyme 188 was from Novozymes (2880 Bagsvaerd, Denmark).

Additional enzymes used in the saccharification process (es) herein were the glycosyl hydrolases (GH) Xyn3, Fv3A, Fv51A and Fv43D. Xyn3 (SEQ ID NO:9) is a GH10 family xylanase from *Trichoderma reesei*, Fv3A (SEQ ID NO:10) is a GH3 family enzyme from *Fusarium verticillioides*, Fv43D (SEQ ID NO:11) is a GH43 family enzyme from *Fusarium verticillioides*, and Fv51A (SEQ ID NO:12) is a GH51 family of enzyme from *Fusarium verticillioides*.

Media.

Corn cob hydrolysate used in the adaptation was prepared first by dilute ammonia pretreatment of ground corn cob. A horizontal Littleford Day 130L reactor vessel containing a jacket for passing steam around the body of the vessel and one of the sides (Littleford Day, Inc., Florence, Ky.) was loaded with milled cob. Vacuum was applied to the vessel to reach 0.1 atm prior to introduction of a 29 wt % ammonium hydroxide solution and water near the top of the vessel to give a 6 wt % $NH_3$ relative to dry weight biomass. Steam was introduced near the top of the vessel to raise the internal vessel temperature to 145° C. This temperature was held for 20 mins. At the end of pretreatment, the reactor was depressurized to reach atmospheric pressure. Vacuum (approximately to less than 1 atm) was subsequently applied to lower the temperature to less than 60° C.

The pretreated cob was then treated with and enzyme consortium allowing for enzymatic hydrolysis of the cellulose and hemicellulose polymers using an enzyme mix containing: Spezyme CP-100 at 34 mg protein per g of glucan in the ptretreated cob; Multifect CX12L at 12.5 mg protein per g of xylan in the pretreated cob; Novozymes 188 at 6.6 mg protein per g glucan in the pretreated cob. The hydrolysis reaction was carried out at 25% (weight/volume) pretreated cob dry matter, pH 5.3 and 47° C. The reaction was stirred continuously and ran for 72 hrs.

Solids were removed from the hydrolysate using an initial, continuous centrifugation to partially clarify the mixture. The partially clarified mix was again centrifuged at 18,000×G for 20 mins then passed first through a 0.45 micron filter followed by a 0.22 micron filter to produce clarified, filter sterilized hydrolysate.

Each of the glucose, xylose and acetate concentrations was determined by HPLC analysis. The clarified hydrolysate had a 68 g/L glucose concentration, 46 g/L xylose concentration, and 5 g/L acetate concentration. The clarified hydrolysate was supplemented with 6.2 g/L ammonium acetate to increase the total ammonium acetate concentration such that the concentration falls within the range of 11 to 12 g/L. Where noted, 0.5% yeast extract (Difco Yeast Extract, Becton, Dickinson and Co., Sparks, Md.) was added to provide additional nutrients. This medium was labeled HYAc/YE. The pH of the HYAc/YE medium was adjusted to 5.8 and the medium was filter sterilized.

A hydrolysate medium for 1 L fermentation test was prepared using the method described above, except that the enzyme composition used in the hydrolysis was changed to an enzyme blend comprising Accellerase® 1500, Xyn3, Fv3A, Fv51A, and Fv43D, which was added to the hydrolysis reaction at 21.3 mg protein/g glucan+xylan. The hydrolysate was used without clarification in the 1 L scale fermentations.

Additional Media

MRM3 contains per liter: yeast extract (10 g), $KH_2PO_4$ (2 g) and $MgSO_4 \cdot 7H_2O$ (1 g)

Figure 2:
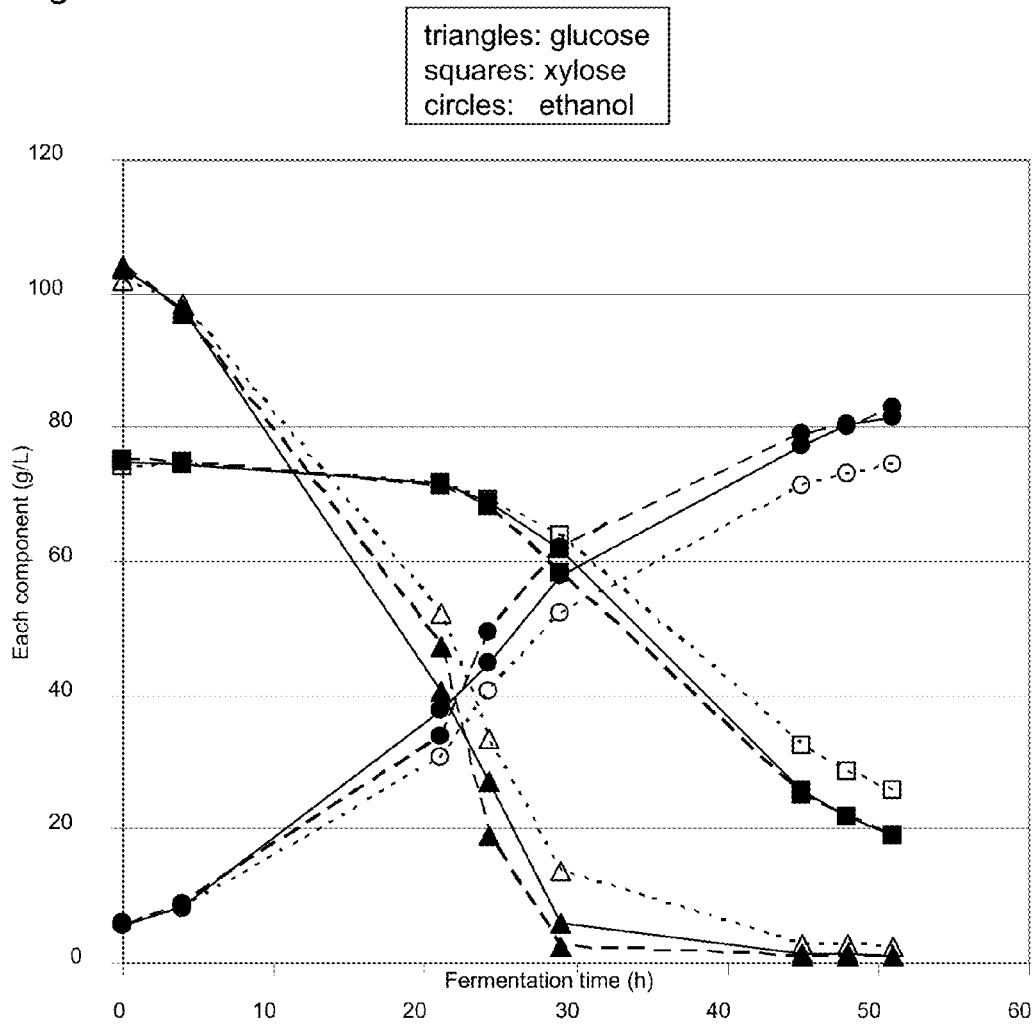
FIG. 2 shows a graph of fermentation of corn cob hydrolysate over time, comparing glucose and xylose utilization and ethanol production for *Zymomonas* strains ZW705, Adapted 7-31, and Adapted 5-6.

MRM3G6.5X4.5NH4Ac12.3 is MRM3 containing 65 g/L glucose, 45 g/L xylose, 12.3 g/L ammonium acetate G5 or MRM3G5 is MRM3 containing 50 g/L glucose G10 or MRM3G10 is MRM3 containing 100 g/L glucose MRM3G2 is MRM3 containing 20 g/L glucose MRM3X2 is MRM3 containing 20 g/l xylose halfYEMaxSM:10 g/L Difo yeast extract, 2 g/L $KH_2PO_4$, 5 g/L $MgSO_4 \cdot 7H_2O$, 10 mM sorbitol, 150 g/L glucose For plating studies noted in FIG. 2, MRM3G2 (20 g/L glucose) and MRM3X2 (20 g/L xylose) were supplemented with 1.5% agar, heated to dissolve the agar, cooled to 45° C. and poured into petri dishes.

Preparation of Frozen Stock Cultures

Frozen stock cultures were prepared for strain ZW705, weekly turbidostat sample population cultures, and isolated mutant clones. Additional frozen stocks were prepared by growing the original frozen stock on G5 or G10 medium and using the biomass generated to prepare new frozen stocks.

Inoculation of Seed, Batch Adaptation and Turbidostat Cultures

Frozen stock was used to inoculate overnight G5 or G10 seed cultures. The seed cultures were used to inoculate batch adaptation cultures by centrifuging the seed culture medium and diluting the cell pellet in fresh adaptation medium. For turbidostat inoculation, the entire seed pellet was re-suspended in 10-15 ml of turbidostat resting medium and used to inoculate the turbidostat reactor or 5 ml of overnight seed was used as a 10% inoculum.

Culture OD600 Measurements

To measure culture OD, samples were diluted in 100 g/L xylose (diluent and blank). The diluted culture was allowed to sit for 15 minutes before taking the OD measurement. All OD measurements were at 600 nm.

HPLC Analysis

HPLC analyses were performed with a Waters Alliance HPLC system. The column used was a Transgenomic ION-300 column (#ICE-99-9850, Transgenomic, Inc) with a Bio-Rad Micro-Guard Cartridge Cation-H (#125-0129, Bio-Rad, Hercules, Calif.). The column was run at 75° C. and 0.4 mL/min flow rate using 0.01 $NH_2SO_4$ as solvent. The concentrations of starting sugars and products were determined with a refractive index detector using external standard calibration curves.

Strain ZW705 Description

*Zymomonas mobilis* strainZW705 was produced from strain ZW804-1. ZW801-4 is a recombinant xylose-utilizing strain of *Z. mobilis* that was described in commonly owned U.S. Pat. No. 7,741,119, which is incorporated herein by reference. Strain ZW801-4 was derived from strain ZW800, which was derived from strain ZW658, all as described in U.S. Pat. No. 7,741,119. ZW658 was constructed by integrating two operons, $P_{gap}$xylAB and $P_{gap}$taltkt, containing four xylose-utilizing genes encoding xylose isomerase, xylulokinase, transaldolase and transketolase, into the genome of ZW1 (ATCC 31821) via sequential transposition events, and followed by adaptation on selective media containing xylose (U.S. Pat. No. 7,629,156). ZW658 was deposited as ATCC PTA-7858. In ZW658, the gene encoding glucose-fructose oxidoreductase was insertionally-inactivated using host-mediated, double-crossover, homologous recombination and spectinomycin resistance as a selectable marker to create ZW800 (U.S. Pat. No. 7,741,119). The spectinomycin resistance marker, which was bounded by loxP sites, was removed by site specific recombination using Cre recombinase to create ZW801-4.

Cultures of *Z. mobilis* strain ZW801-4 were adapted for growth under stress conditions of medium containing ammonium acetate to produce ZW705 as described in commonly owned United States Patent Publication US20110014670A1, which is incorporated herein by reference. A continuous culture of ZW801-4 was run in 250 ml stirred, pH and temperature controlled fermentors (Sixfors; Bottmingen, Switzerland). The basal medium for fermentation was 5 g/L yeast extract, 15 mM ammonium phosphate, 1 g/L magnesium sulfate, 10 mM sorbitol, 50 g/L xylose and 50 g/L glucose. Adaptation to growth in the presence of high concentrations of acetate and ammonia was effected by gradually increasing the concentration of ammonium acetate added to the above continuous culture media while maintaining an established growth rate as measured by the specific dilution rate over a period of 97 days. Ammonium acetate was increased to a concentration of 160 mM. Further increases in ammonium ion concentration were achieved by addition of ammonium phosphate to a final total ammonium ion concentration of 210 mM by the end of 139 days of continuous culture. Strain ZW705 was isolated from the adapted population by plating to single colonies and amplification of one chosen colony.

Example 1

Adaptation to Corn Cob Hydrolysate Using an Automated, Cell Density Controlled Continuous Culture Apparatus The turbidostat described in General Methods was used to adapt *Zymomonas mobilis* cultures to growth in corn cob hydrolysate medium. A culture of strain ZW705 was grown in the turbidostat described in General Methods to an arbitrary turbidity set point that dictated that the culture use all of the glucose and approximately half of the xylose present in the incoming media to meet the set point cell density at the set dilution rate. Using resting medium that was 50% HYAc/YE and 50% MRM3G6.5X4.5$NH_4$Ac12.3. The turbidostat was run as described in General Methods using as challenge medium HYAc/YE. Cell samples were taken weekly for 6 weeks from the trap chamber.

After 6 weeks of continuous culture, samples from the weekly saved cell stocks were revived in MRM3G6 and grown to about 1 OD600 in 10 ml static cultures at 33° C. These were used to inoculate 12 ml cultures of HYAc/YE medium to approximately 0.4 OD600 nm, and the cultures were grown at 30° C. Samples were taken at different times as in Table 1, and assayed for OD600, sugar consumption, and ethanol production. The results are shown in Table 1.

TABLE 1

Analysis of weekly trubidostat samples grown in 12 ml HYAc/YE fermentations

| culture | Sampling time | OD 600 nm | remaining glucose (g/L) | remaining xylose (g/L) | ethanol (g/L) |
|---|---|---|---|---|---|
| ZW705 | 0 | 0.400 | 69.8 | 46.0 | 0.0 |
|  | 24 | 0.760 | 52.8 | 45.4 | 8.4 |
|  | 48 | 2.140 | 5.4 | 30.7 | 38.2 |
|  | 72 | 2.300 | 2.3 | 16.0 | 45.1 |
| week 1 | 0 | 0.417 | 69.8 | 46.0 | 0.0 |
|  | 24 | 0.78 | 48.8 | 45.6 | 9.7 |
|  | 48 | 1.430 | 4.8 | 34.2 | 35.6 |
|  | 72 | 1.890 | 2.4 | 25.7 | 37.7 |
| week 2 | 0 | 0.351 | 69.8 | 46.0 | 0.0 |
|  | 24 | 0.810 | 53.2 | 46.1 | 7.7 |
|  | 48 | 1.670 | 7.6 | 36.1 | 33.5 |
|  | 72 | 1.710 | 2.7 | 26.6 | 39.3 |
| week 3 | 0 | 0.395 | 69.8 | 46.0 | 0.0 |
|  | 24 | 1.090 | 42.9 | 44.3 | 13.4 |
|  | 48 | 1.920 | 2.9 | 27.3 | 40.2 |
|  | 72 | 2.410 | 1.9 | 19.7 | 42.1 |
| week 4 | 0 | 0.386 | 69.8 | 46.0 | 0.0 |
|  | 24 | 1.070 | 42.2 | 44.2 | 13.7 |
|  | 48 | 1.510 | 3.3 | 30.7 | 38.4 |
|  | 72 | 2.010 | 2.1 | 25.2 | 39.4 |
| week 5 | 0 | 0.328 | 69.8 | 46.0 | 0.0 |
|  | 24 | 0.920 | 52.7 | 45.5 | 7.7 |
|  | 48 | 1.350 | 8.5 | 36.2 | 34.1 |
|  | 72 | 1.650 | 2.9 | 25.8 | 40.4 |
| week 6 | 0 | 0.402 | 69.8 | 46.0 | 0.0 |
|  | 24 | 0.600 | 55.5 | 45.9 | 6.9 |
|  | 48 | 1.360 | 13.9 | 39.8 | 29.1 |
|  | 72 | 1.530 | 4.1 | 31.6 | 37.5 |

All cultures retained the ability to grow on xylose but the rate of xylose use seemed to have decreased after the $3^{rd}$ week of adaptation. Single colonies were isolated from the culture of cells sampled at the end of week 3. Colonies were isolated by growing the retained glycerol stock in MRM3G5, then plating on MRM3X2 plates. Single colonies were replica patched onto MRM3X2 and MRM3G2 plates. Large, dense patches on both carbon sources were chosen as strains and maintained as frozen glycerol stocks. Selected strains were grown in 12 ml test cultures as described for the frozen stock population test described above. Results for six strains and ZW705 are shown in Table 2.

TABLE 2

Analysis of isolated pure cultures from week 3 of the turbidostat adaptation of ZW705 grown in 12 ml HYAc/YE fermentations

| Strain | Sampling time | OD 600 nm | remaining glucose (g/L) | remaining xylose (g/L) | ethanol (g/L) |
|---|---|---|---|---|---|
| ZW705 | 0 | 0.383 | 74.9 | 44.4 | 0.0 |
|  | 24 | 0.450 | 51.1 | 43.4 | 13.4 |
|  | 48 | 1.350 | 5.7 | 35.1 | 31.4 |
|  | 72 | 2.770 | 1.9 | 17.1 | 49.0 |
| 12-18X-1-10 | 0 | 0.333 | 74.9 | 44.4 | 0.0 |
|  | 24 | 0.760 | 47.7 | 44.4 | 14.6 |
|  | 48 | 2.530 | 3.1 | 28.3 | 36.7 |
|  | 72 | 2.800 | 1.7 | 12.1 | 50.4 |
| 12-18X-2-36 | 0 | 0.400 | 74.9 | 44.4 | 0.0 |
|  | 24 | 0.900 | 46.9 | 44.3 | 15.1 |
|  | 48 | 2.220 | 2.8 | 24.2 | 38.9 |
|  | 72 | 3.430 | 1.8 | 9.1 | 53.3 |
| 12-18X-5-34 | 0 | 3.820 | 74.9 | 44.4 | 0.0 |
|  | 24 | 0.530 | 52.7 | 44.9 | 13.1 |
|  | 48 | 2.430 | 4.3 | 30.3 | 35.7 |
|  | 72 | 3.050 | 1.9 | 13.0 | 51.1 |
| 12-18X-6-9 | 0 | 0.401 | 74.9 | 44.4 | 0.0 |
|  | 24 | 0.530 | 51.2 | 44.4 | 13.1 |
|  | 48 | 2.590 | 3.2 | 28.7 | 36.6 |
|  | 72 | 3.050 | 1.8 | 11.4 | 52.5 |
| 12-18X-7-43 | 0 | 0.351 | 74.9 | 44.4 | 0.0 |
|  | 24 | 0.600 | 49.6 | 43.9 | 14.3 |
|  | 48 | 2.200 | 3.1 | 26.9 | 38.3 |
|  | 72 | 3.330 | 1.7 | 9.9 | 53.8 |
| 12-18X-8-19 | 0 | 0.409 | 74.9 | 44.4 | 0.0 |
|  | 24 | 0.749 | 45.2 | 44.4 | 16.0 |
|  | 48 | 2.230 | 3.4 | 27.3 | 34.8 |
|  | 72 | 2.910 | 1.7 | 11.7 | 52.1 |

All of the selected strains produced more ethanol in the 12 ml test than did the strain that entered adaptation (ZW705). The strains used slightly more xylose than the parent strain. Strain 12-18X-2-36 was chosen for an additional round of adaptation.

Example 2

Adaptation to Corn Cob Hydrolysate with Added Ethanol Using an Automated, Cell Density Controlled Continuous Culture Apparatus A culture of strain 12-18X-2-36 (described in Example 1) was grown in the turbidostat as described above for strain ZW705 and in General Methods, except that the resting medium was HYAc/YE and the challenge medium was HYAc/YE+9 weight % ethanol. The turbidostat was run for 4 weeks with weekly sampling of the chamber outflow. Frozen cell stocks were made from the outflow samples. Frozen cell stocks were revived in MRM3G6 for testing in 12 ml hydrolysate fermentations under the same conditions as described for the first turbidostat run, but with starting density of about 0.5 OD600. One fermentation was in the same HYAc/YE medium, and another fermentation was in HYAc/YE to which ethanol was added at 30 g per L of medium. Results for both fermentations are shown in Table 3.

TABLE 3

Analysis of weekly trubidostat samples grown in 12 ml HYAc/YE or HYAc/YE + 30 g/L ethanol fermentations

| | | HYAc/YE with no added ethanol | | | | HYAc/YE with 30 g/L ethanol | | | |
|---|---|---|---|---|---|---|---|---|---|
| culture | sampling time | OD 600 nm | remaining glucose (g/L) | remaining xylose (g/L) | ethanol (g/L) | OD 600 nm | remaining glucose (g/L) | remaining xylose (g/L) | ethanol (g/L) |
| ZW705 | 0 | 0.530 | 75.5 | 47.7 | 0.0 | 0.530 | 73.3 | 48.3 | 26.2 |
|  | 24 | 0.890 | 50.1 | 48.0 | 13.7 | 0.470 | 63.6 | 46.8 | 27.3 |
|  | 48 | 2.200 | 3.9 | 33.6 | 43.6 | 0.760 | 51.1 | 45.7 | 32.7 |
|  | 72 | 2.500 | 1.8 | 19.7 | 50.3 | 1.060 | 39.0 | 45.7 | 39.6 |
| week 1 | 0 | 0.513 | 75.5 | 47.7 | 0.0 | 0.515 | 73.3 | 48.3 | 26.2 |
|  | 24 | 1.360 | 20.1 | 44.2 | 30.2 | 1.370 | 45.2 | 46.9 | 36.3 |
|  | 48 | 2.200 | 2.1 | 27.3 | 47.7 | 1.810 | 14.7 | 42.5 | 50.1 |
|  | 72 | 2.520 | 1.7 | 18.5 | 50.6 | 1.920 | 3.8 | 40.1 | 57.7 |
| week 2 | 0 | 0.504 | 75.5 | 47.7 | 0.0 | 0.504 | 73.3 | 48.3 | 26.2 |
|  | 24 | 1.140 | 32.4 | 47.1 | 23.2 | 0.950 | 51.6 | 46.8 | 34.1 |
|  | 48 | 1.910 | 2.4 | 27.8 | 47.7 | 1.500 | 19.4 | 42.8 | 50.4 |
|  | 72 | 2.290 | 1.7 | 18.5 | 51.4 | 1.780 | 5.7 | 38.0 | 60.5 |
| week 3 | 0 | 0.527 | 75.5 | 47.7 | 0.0 | 0.527 | 73.3 | 48.3 | 26.2 |
|  | 24 | 0.640 | 53.5 | 48.7 | 12.3 | 0.570 | 62.1 | 48.2 | 28.5 |
|  | 48 | 1.420 | 7.3 | 37.7 | 39.5 | 0.600 | 51.9 | 46.1 | 33.2 |
|  | 72 | 2.010 | 2.0 | 25.5 | 47.3 | 1.060 | 35.3 | 44.8 | 38.7 |
| week 4 | 0 | 0.518 | 75.5 | 47.7 | 0.0 | 0.518 | 73.3 | 48.3 | 26.2 |
|  | 24 | 0.730 | 25.5 | 45.2 | 27.8 | 0.480 | 64.3 | 47.7 | 25.5 |
|  | 48 | 1.760 | 2.3 | 23.7 | 49.3 | 0.560 | 52.8 | 46.8 | 32.9 |
|  | 72 | 1.890 | 1.8 | 15.8 | 52.6 | 1.080 | 38.4 | 45.2 | 40.4 |

All cultures were similar to the ZW705 control in the test fermentations with no ethanol added to the HYAc/YE medium. In fermentations with 30 g/L ethanol added to the HYAc/YE medium, the cultures taken after weeks 1 and 2 were much better at utilizing glucose and producing ethanol than ZW705 and the week 3 and 4 samples. The culture stored after week 2 had the highest ending ethanol titer in the test that began with added ethanol and was chosen for isolation of single cell derived strains. The strain isolation procedure described for the screen that derived strain 12-18X-2-36 was run twice and the results of both rounds of screening are shown in Tables 4 and 5. Screens were started in HYAc/YE medium with no added ethanol, or with 40 g/L added ethanol.

TABLE 4

Analysis of isolated pure cultures from week 2 of the turbidosat adaptation of 12-18X-2-36 grown in 12 ml HYAc/YE or HYAc/YE + ethanol fermentations (round 1)

| | | HYAc/YE with no added ethanol | | | | HYAc/YE with 40 g/L ethanol | | | |
| --- | --- | --- | --- | --- | --- | --- | --- | --- | --- |
| culture | Sampling time | OD 600 nm | remaining glucose (g/L) | Remaining xylose (g/L) | ethanol (g/L) | OD 600 nm | Remaining glucose (g/L) | Remaining xylose (g/L) | ethanol (g/L) |
| ZW705 | 0.0 | 0.5 | 77.7 | 50.9 | 0.0 | 0.50 | 75.1 | 49.2 | 28.1 |
| | 24.0 | 0.8 | 56.5 | 50.2 | 9.0 | 0.42 | 69.8 | 50.0 | 24.5 |
| | 48.0 | 1.8 | 12.6 | 41.6 | 28.2 | 0.75 | 62.6 | 49.6 | 27.5 |
| | 72.0 | 1.9 | 3.8 | 24.0 | 46.7 | 0.60 | 52.7 | 48.7 | 36.5 |
| 1-32 | 0.0 | 0.5 | 77.7 | 50.9 | 0.0 | 0.50 | 75.1 | 49.2 | 28.1 |
| | 24.0 | 0.8 | 55.3 | 49.6 | 12.0 | 0.41 | 65.3 | 48.0 | 35.2 |
| | 48.0 | 1.9 | 7.8 | 38.5 | 39.1 | 0.68 | 57.3 | 47.6 | 38.2 |
| | 72.0 | 2.4 | 2.6 | 21.2 | 51.6 | 0.72 | 50.8 | 47.5 | 41.0 |
| 1-44 | 0.0 | 0.5 | 77.7 | 50.9 | 0.0 | 0.50 | 75.1 | 49.2 | 28.1 |
| | 24.0 | 0.8 | 53.7 | 49.9 | 12.6 | 0.44 | 66.7 | 48.2 | 34.7 |
| | 48.0 | 1.9 | 6.5 | 37.5 | 40.1 | 0.75 | 60.8 | 48.5 | 35.5 |
| | 72.0 | 2.2 | 1.8 | 21.7 | 50.1 | 0.65 | 55.8 | 48.1 | 37.4 |
| 2-24 | 0.0 | 0.5 | 77.7 | 50.9 | 0.0 | 0.50 | 75.1 | 49.2 | 28.1 |
| | 24.0 | 0.7 | 59.4 | 49.7 | 9.8 | 0.41 | 67.6 | 48.6 | 32.0 |
| | 48.0 | 1.9 | 4.8 | 34.9 | 42.8 | 0.69 | 61.2 | 48.6 | 34.2 |
| | 72.0 | 2.3 | 2.5 | 18.6 | 51.3 | 0.64 | 55.9 | 48.6 | 36.9 |
| 2-47 | 0.0 | 0.5 | 77.7 | 50.9 | 0.0 | 0.50 | 75.1 | 49.2 | 28.1 |
| | 24.0 | 0.9 | 52.1 | 49.5 | 13.5 | 0.49 | 66.3 | 48.7 | 30.8 |
| | 48.0 | 1.8 | 9.6 | 40.3 | 37.0 | 0.90 | 58.6 | 48.8 | 34.4 |
| | 72.0 | 1.8 | 2.7 | 27.6 | 46.3 | 0.61 | 51.8 | 48.4 | 38.2 |
| 3-8 | 0.0 | 0.5 | 77.7 | 50.9 | 0.0 | 0.50 | 75.1 | 49.2 | 28.1 |
| | 24.0 | 0.8 | 56.9 | 49.8 | 10.9 | 0.44 | 66.6 | 48.0 | 33.8 |
| | 48.0 | 2.0 | 50.0 | 34.3 | 43.0 | 0.76 | 58.3 | 47.9 | 37.2 |
| | 72.0 | 2.4 | 2.6 | 19.6 | 50.7 | 0.85 | 50.6 | 47.7 | 40.8 |
| 3-45 | 0.0 | 0.5 | 77.7 | 50.9 | 0.0 | 0.50 | 75.1 | 49.2 | 28.1 |
| | 24.0 | 0.6 | 60.4 | 950.0 | 9.2 | 0.44 | 67.6 | 48.4 | 34.3 |
| | 48.0 | 1.3 | 14.1 | 43.4 | 33.6 | 0.55 | 61.4 | 48.1 | 36.7 |
| | 72.0 | 1.8 | 2.6 | 19.6 | 45.1 | 0.52 | 57.2 | 47.9 | 38.0 |
| 4-17 | 0.0 | 0.5 | 77.7 | 50.9 | 0.0 | 0.50 | 75.1 | 49.2 | 28.1 |
| | 24.0 | 0.6 | 58.8 | 49.6 | 10.0 | 0.44 | 66.7 | 48.3 | 32.8 |
| | 48.0 | 1.4 | 5.7 | 38.0 | 40.4 | 0.60 | 59.7 | 48.4 | 34.8 |
| | 72.0 | 1.9 | 2.4 | 29.6 | 49.6 | 0.54 | 55.2 | 48.6 | 35.5 |
| 4-27 | 0.0 | 0.5 | 77.7 | 50.9 | 0.0 | 0.50 | 75.1 | 49.2 | 28.1 |
| | 24.0 | 0.8 | 49.8 | 49.4 | 14.6 | 0.52 | 63.6 | 48.4 | 33.7 |
| | 48.0 | 1.6 | 4.3 | 34.1 | 44.0 | 0.74 | 53.8 | 48.2 | 37.9 |
| | 72.0 | 2.1 | 2.6 | 23.7 | 48.1 | 0.68 | 47.5 | 48.1 | 40.3 |
| <u>5-6</u> | 0.0 | 0.5 | 77.7 | 50.9 | 0.0 | 0.50 | 75.1 | 49.2 | 28.1 |
| | 24.0 | 0.6 | 53.9 | 79.7 | 12.6 | 0.46 | 59.7 | 48.7 | 35.5 |
| | 48.0 | 1.8 | 5.8 | 36.9 | 41.9 | 0.90 | 47.7 | 48.8 | 40.3 |
| | 72.0 | 1.9 | 2.7 | 23.8 | 48.7 | 0.59 | <u>41.5</u> | 48.6 | <u>42.9</u> |
| 5-35 | 0.0 | 0.5 | 77.7 | 50.9 | 0.0 | 0.50 | 75.1 | 49.2 | 28.1 |
| | 24.0 | 0.8 | 52.7 | 49.7 | 13.1 | 0.42 | 65.8 | 48.2 | 33.3 |
| | 48.0 | 1.7 | 5.7 | 36.8 | 41.6 | 0.74 | 58.4 | 48.0 | 36.3 |
| | 72.0 | 1.9 | 2.4 | 22.7 | 49.6 | 0.80 | 53.6 | 48.1 | 38.1 |

When starting without added ethanol most strains used all of the glucose in the hydrolysate medium but did not use all of the xylose, so that total ethanol production was dependent on the extent of xylose utilization. Several strains used more xylose and produced more ethanol than did the non-adapted parent strain ZW705. When 40 g/L ethanol was added to the starting medium, growth and sugar utilization was much less in all strains. In this test xylose use was very low or xylose was not consumed at all in most cases. Three strains used significantly more glucose and produced more ethanol than ZW705. The best of those was the strain Adapted 5-6, shown in Table 4.

TABLE 5

Analysis of isolated pure cultures from week 2 of the turbidosat adaptation of 12-18X-2-36 grown in 12 ml HYAc/YE or HYAc/YE + ethanol fermentations (round 2)

| | | HYAc/YE with no added ethanol | | | | HYAc/YE with 40 g/L ethanol | | | |
|---|---|---|---|---|---|---|---|---|---|
| culture | Sampling time | OD 600 nm | remaining glucose (g/L) | remaining xylose (g/L) | ethanol (g/L) | OD 600 nm | remaining glucose (g/L) | remaining xylose (g/L) | ethanol (g/L) |
| ZW705 | 0.0 | 0.5 | 77.8 | 51.5 | 0.0 | 0.50 | 74.9 | 49.1 | 30.6 |
| | 24.0 | 0.9 | 40.7 | 48.6 | 19.0 | 0.60 | 56.2 | 49.0 | 34.0 |
| | 48.0 | 2.5 | 2.9 | 26.5 | 48.3 | 1.14 | 28.4 | 46.9 | 48.8 |
| | 72.0 | 2.9 | 2.2 | 17.9 | 52.7 | 1.49 | 17.5 | 44.7 | 55.3 |
| 6-4 | 0.0 | 0.5 | 77.8 | 51.5 | 0.0 | 0.50 | 74.9 | 49.1 | 30.6 |
| | 24.0 | 0.9 | 19.0 | 46.0 | 30.6 | 0.79 | 54.4 | 49.0 | 34.9 |
| | 48.0 | 2.4 | 2.9 | 28.4 | 47.2 | 1.75 | 18.9 | 44.2 | 55.2 |
| | 72.0 | 2.6 | 2.1 | 18.4 | 51.8 | 1.98 | 9.2 | 39.8 | 61.7 |
| 6-43 | 0.0 | 0.5 | 77.8 | 51.5 | 0.0 | 0.50 | 74.9 | 49.1 | 30.6 |
| | 24.0 | 1.3 | 28.0 | 47.7 | 25.0 | 0.52 | 58.6 | 48.3 | 36.5 |
| | 48.0 | 2.7 | 2.7 | 20.9 | 50.5 | 0.65 | 44.9 | 47.6 | 44.0 |
| | 72.0 | 2.8 | 2.2 | 14.6 | 52.9 | 1.12 | 37.9 | 47.3 | 46.8 |
| 7-13 | 0.0 | 0.5 | 77.8 | 51.5 | 0.0 | 0.50 | 74.9 | 49.1 | 30.6 |
| | 24.0 | 1.6 | 17.5 | 46.6 | 29.7 | 0.51 | 57.0 | 48.2 | 38.0 |
| | 48.0 | 32.7 | 2.6 | 18.2 | 50.6 | 0.99 | 35.7 | 46.3 | 49.4 |
| | 72.0 | 3.3 | 2.2 | 11.8 | 53.3 | 1.99 | 25.9 | 44.9 | 53.8 |
| <u>7-31</u> | 0.0 | 0.5 | 77.8 | 51.5 | 0.0 | 0.50 | 74.9 | 49.1 | 30.6 |
| | 24.0 | 1.4 | 23.1 | 46.9 | 27.7 | 0.77 | 39.5 | 48.0 | 39.5 |
| | 48.0 | 2.5 | 2.7 | 19.2 | 52.3 | 1.35 | 22.3 | 45.2 | 56.7 |
| | 72.0 | 3.0 | 2.1 | 12.8 | 53.7 | 2.09 | 12.7 | 43.6 | 56.5 |
| 8-2 | 0.0 | 0.5 | 77.8 | 51.5 | 0.0 | 0.50 | 74.9 | 49.1 | 30.6 |
| | 24.0 | 1.5 | 22.1 | 47.5 | 20.7 | 0.59 | 54.8 | 48.3 | 37.8 |
| | 48.0 | 3.3 | 2.8 | 20.3 | 50.3 | 1.24 | 30.4 | 46.3 | 51.7 |
| | 72.0 | 3.4 | 2.3 | 14.8 | 51.8 | 1.14 | 20.4 | 44.8 | 55.0 |
| 8-22 | 0.0 | 0.5 | 77.8 | 51.5 | 0.0 | 0.50 | 74.9 | 49.1 | 30.6 |
| | 24.0 | 1.2 | 28.7 | 47.6 | 24.6 | 0.56 | 58.1 | 48.6 | 35.5 |
| | 48.0 | 2.3 | 2.8 | 19.2 | 51.5 | 0.99 | 33.6 | 46.4 | 49.2 |
| | 72.0 | 2.8 | 2.2 | 11.4 | 55.2 | 1.14 | 21.7 | 44.1 | 54.9 |
| 9-5 | 0.0 | 0.5 | 77.8 | 51.5 | 0.0 | 0.50 | 74.9 | 49.1 | 30.6 |
| | 24.0 | 1.3 | 32.0 | 49.2 | 23.0 | 0.67 | 57.9 | 48.2 | 37.0 |
| | 48.0 | 2.5 | 2.9 | 23.0 | 48.8 | 1.07 | 32.0 | 46.2 | 51.8 |
| | 72.0 | 2.7 | 2.3 | 14.7 | 52.4 | 1.68 | 22.2 | 44.3 | 55.6 |
| 9-21 | 0.0 | 0.5 | 77.8 | 51.5 | 0.0 | 0.50 | 74.9 | 49.1 | 30.6 |
| | 24.0 | 1.4 | 28.4 | 48.0 | 24.9 | 0.51 | 58.7 | 48.3 | 35.9 |
| | 48.0 | 2.6 | 2.7 | 21.1 | 50.4 | 0.88 | 36.4 | 47.0 | 48.4 |
| | 72.0 | 2.7 | 2.3 | 13.4 | 53.5 | 1.06 | 26.1 | 45.3 | 52.2 |
| 10-17 | 0.0 | 0.5 | 77.8 | 51.5 | 0.0 | 0.50 | 74.9 | 49.1 | 30.6 |
| | 24.0 | 0.9 | 42.1 | 49.4 | 18.4 | 0.32 | 62.8 | 48.4 | 33.9 |
| | 48.0 | 2.4 | 3.0 | 24.7 | 49.0 | 0.43 | 51.7 | 47.8 | 41.2 |
| | 72.0 | 2.8 | 2.3 | 14.0 | 52.7 | 0.55 | 45.6 | 47.7 | 41.0 |
| 10-32 | 0.0 | 0.5 | 77.8 | 51.5 | 0.0 | 0.50 | 74.9 | 49.1 | 30.6 |
| | 24.0 | 1.1 | 37.6 | 48.9 | 20.1 | 0.50 | 59.3 | 48.4 | 34.1 |
| | 48.0 | 2.3 | 2.8 | 23.4 | 47.3 | 1.05 | 35.2 | 46.9 | 46.6 |
| | 72.0 | 2.4 | 2.3 | 15.7 | 51.0 | 1.34 | 22.6 | 45.0 | 52.3 |

Results were similar in the second strain isolation experiment. Several strains used more xylose than ZW705 in the no added ethanol test, and used more glucose in the added ethanol test. Many used more glucose in the first 24 hours of growth and achieved higher cell mass as measured by OD600 nm in the first 24 hours also. Of these, the strain Adapted 7-31 was chosen for further testing.

Example 3

Performance Testing of Hydrolysate Adapted Strains

Seed Fermentation

Seed fermentation was performed in a 1 L fermenter (Sartorious Stedim BIOSTAT). Sterilized, empty fermenters were filled with filter-sterilized halfYEMaxSM. Seed fermentations were performed at 33° C. and pH 5.5, using unfiltered 4 N NH$_4$OH as the base to control to pH 5.5. Seed fermentations were inoculated with sufficient volume of frozen stock cells that were grown for about 7.5 hr to OD600 of about 2.5, in halfYEMaxSM. Cells were diluted into the 1L fermenter to give a starting OD600 nm of about 0.025. In general, seed fermentations were harvested when ~120 g/L glucose had been consumed and/or OD600 of about 10 had been reached. The seed fermentations were periodically sampled to monitor growth, and harvested at about 18.5 hr.

Hydrolysate Fermentation

Hydrolysate fermentation was performed in a 1 L fermentor (Sartorious Stedim BIOSTAT). Sterilized, empty fermentors were filled with 450 ml of corn cob hydrolysate prepared as described in General Methods. Hydrolysate fermentations were performed at pH 5.8 using unfiltered 4 N NaOH as the base to adjust pH. Hydrolysate fermentation began at 33° C. Hydrolysate fermentations were inoculated with 10 volume % (50 ml) of seed from the seed fermentation (see above) to generate an initial OD of about 1.0. The hydrolysate fermentations were periodically sampled to monitor reaction progress. The samples were assayed for glucose, xylose and ethanol as described in General Methods.

Two hydrolysate fermentations were run one week apart, each with the control strain ZW705 and the selected strain from adaptation, Adapted 7-31 (Example 2). The time course of the fermentations is shown in FIG. 1. Adapted 7-31 used glucose faster than ZW705 and used more total xylose to achieve a higher ethanol titer during the course of the fermentation.

Hydrolysate fermentations were run and assayed as described above to compare the control strain ZW705, strain Adapted 7-31, and strain Adapted 5-6 (see Example 2). Results are shown in FIG. 2. Strain Adapted 5-6 performance was equivalent to that of strain Adapted 7-31. Both of these adapted strains achieved a higher final ethanol titer by using glucose more rapidly at the beginning of the fermentation and by using more xylose by the end of the fermentation.

Example 4

Comparative DNA Sequencing of Adapted Strains

The whole genome sequence of wild type *Zymomonas mobilis* (ZM4) has been described (Jeong-Sun Seo et. al, Nature Biotechnology. 23, 2005). A wild type starting strain (ZW1; ATCC 31821), an intermediate strain (ZW658; ATCC PTA-7858) and ZW705, were sequenced using high throughput 454 technology (Shendure and Ji, Nature Biotech. 26:1135 (2008)) and compared to the published wild type sequence. Strains Adapted 5-6 and Adapted 7-31 were sequenced using Ilumina technology (Shendure and Ji, Nature Biotech 26:1135 (2008)). From the wild type sequence, the sequence of ZW658 and the separately determined insertion sites of the intentional sequence changes coming from insertion of the two xylose utilization operons and the knockout of the GFOR gene (described in General Methods), a consensus sequence was made to which sequences from adapted strains could be compared. The description of sequencing and genome assembly follows.

Sequencing

Strains were sequenced using the sequencing technologies Illumina/Solexa and Roche-454. These massively parallel sequencing methods give very high throughput of short reads. In the case of Illumina, it gives more than 200 million reads that are 100 bp long. For Roche-454 outputs 1 million reads are 500 bp long. Both methods allow sequencing from both ends of genomic DNA fragments to produce paired-end reads Hundreds of millions of short reads from Adapted 5-6 and Adapted 7-31 strains were aligned to a reference genome sequence prepared from the wild type, ZW658, and ZW705 sequences. The resulting alignment was analyzed to collect information on coverage and variations. Since many reads can align to a specific region, the alignment is a pile up of reads against the reference and the depth coverage of a given position is the number of reads that cover that position. If at a position the consensus base is different from the reference base, the position is said to have a Single Nucleotide Polymorphism (SNP) variation.

In the comparison of the Adapted 5-6 and Adapted 7-31 sequences to the starting strain for adaptation ZW705 sequence, a single base change, or SNP, was identified for each adapted strain. The SNP for Adapted 5-6 was at position 1453116 which is in the open reading frame of a gene designated zmo1330. The SNP for Adapted 7-31 was in the same open reading frame, but the change was at a different position (1453863). The change in Adapted 5-6 is in position 1097 of the coding region (SEQ ID NO:1) and is a change from C to G at that position. This mutation results in a codon change for amino acid 366 from ACA to AGA, resulting in a change in amino acid 366 from threonine to arginine in the encoded protein. The change in Adapted 7-31 is in position 350 of the coding region (SEQ ID NO:1) and is a change from C to T at that position. This mutation results in a codon change for amino acid 117 from TCT to TTT resulting in a change in amino acid 117 from serine to phenylalanine.

The protein encoded by zmo1330 was used in a BLAST of the transporter classification data base (Saier Lab Bioinformatics Group; Saier et al. (2009), Nucl. Acids Res., 37: D274-8) which identified the protein as belonging to the aaeB family. This family of proteins is characterized by having a hydrophobic N terminus that predicts 5 to 6 membrane crosses, a fairly long and less hydrophobic middle section, and then a similar 5 to 6 membrane crosses in the C-terminus. This result suggested that the zmo1330 encoded protein is a membrane transport protein.

In the published *Z. mobilis* genome sequence (Seo et al., ibid; NCBI Reference: NC_006526.2), zmo1330 corresponds to zmo1432 which is annotated as encoding a "fusaric acid resistance protein". The set of proteins required for resistance to fusaric acid in *Pseudomonas cepacia* was identified by Utsumi et al. (Agric. Biol. Chem. 55:1919-1918 (1991)). Among the set of open reading frames (ORFS) in what appeared to be one operon conferring fusaric acid resistance is one designated fusB by Utsumi et al. (ibid) The sequence of the protein encoded by fusB is identical to Bcenm03_1426 from *Burkholderia cenocepacia* (SEQ ID NO:7), which was aligned with the protein encoded by zmo1432. The two protein sequences align with 3 small gaps and are 22% identical, but 63% similar (Clustal W alignment) as shown in FIG. 3. The sequence of Bcenm03_1426 has about the same identity and similarity to the sequence of AaeB (SEQ ID NO:8), which is the larger of two proteins encoded in an operon in *E. coli* that were shown to be required for tolerance to p-aminobenzoic acid (pABA) (VanDyk et al J. Bact. 186:7196-7204 (2004)). Zmo1432 is 17% identical and 55% similar to *E. coli* aaeB. Alignment of proteins encoded by zmo1432 and to aaeB is shown in FIG. 4.

What is claimed is:

1. A recombinant, xylose-utilizing, ethanol-producing microorganism of the genus *Zymomonas*, having at least one genetic modification in the zmo1432 open reading frame, wherein said zmo1432 open reading frame having at least one genetic modification encodes a polypeptide having an amino acid sequence with at least about 95% identity to the amino acid sequence as set forth in SEQ ID NO:2, wherein the presence of the mutant protein increases ethanol production by the *Zymomonas* during fermentation in biomass hydrolysate medium as compared to production by a *Zymomonas* lacking the genetic modification under the same conditions.

2. The recombinant *Zymomonas* of claim 1 wherein the genetic modification is a mutation in the zmo1432 coding region that results in an amino acid substitution selected from the group consisting of: 1) a substitution at position 366 in SEQ ID NO: 2 of arginine for threonine; and 2) a substitution at position 117 in SEQ ID NO: 2 of phenylalanine for serine.

3. The recombinant *Zymomonas* of claim 1 having a higher tolerance to biomass hydrolysate as compared with a *Zymomonas* lacking the at least one genetic modification in the zmo1432 open reading frame.

4. A polynucleotide encoding a protein having the amino acid sequence selected from the group consisting of SEQ ID NO:3 and SEQ ID NO: 4.

5. A method for the production of a recombinant *Zymomonas* ethanologen comprising:
   a) providing a xylose-utilizing, ethanol-producing microorganism of the genus *Zymomonas* comprising a zmo1432 open reading frame encoding a polypeptide having the amino acid sequence as set forth in SEQ ID NO: 2; and
   b) introducing a mutation in the zmo1432 open reading frame of a) such that expression of the mutated open reading frame expresses a polypeptide having an amino acid sequence selected from the group consisting of SEQ ID NO:3 and SEQ ID NO:4.

6. A method of the production of ethanol comprising:
   a) providing the recombinant *Zymomonas* of claim 1;
   b) providing a biomass hydrolysate medium comprising xylose; and
   c) growing the *Zymomonas* of a) in the biomass hydrolysate medium of b) wherein ethanol is produced.

* * * * *